United States Patent
Barnett

(10) Patent No.: US 9,848,954 B2
(45) Date of Patent: Dec. 26, 2017

(54) SURGICAL SYSTEM AND RELATED METHODS

(71) Applicant: Corbin E. Barnett, Lake Mary, FL (US)

(72) Inventor: Corbin E. Barnett, Lake Mary, FL (US)

(*) Notice: Subject to any disclaimer, the term of this patent is extended or adjusted under 35 U.S.C. 154(b) by 262 days.

(21) Appl. No.: 14/577,500

(22) Filed: Dec. 19, 2014

(65) Prior Publication Data

US 2015/0173837 A1   Jun. 25, 2015

Related U.S. Application Data

(60) Provisional application No. 61/918,846, filed on Dec. 20, 2013.

(51) Int. Cl.
| | | |
|---|---|---|
| A61B 34/00 | (2016.01) | |
| A61B 17/00 | (2006.01) | |
| A61B 17/34 | (2006.01) | |
| A61B 90/00 | (2016.01) | |

(52) U.S. Cl.
CPC .............. *A61B 34/70* (2016.02); *A61B 34/71* (2016.02); *A61B 17/00491* (2013.01); *A61B 17/3478* (2013.01); *A61B 2017/003* (2013.01); *A61B 2017/0065* (2013.01); *A61B 2017/00084* (2013.01); *A61B 2017/00207* (2013.01); *A61B 2017/00247* (2013.01); *A61B 2017/00398* (2013.01); *A61B 2034/741* (2016.02); *A61B 2034/742* (2016.02); *A61B 2090/3784* (2016.02)

(58) Field of Classification Search
CPC .... A61M 25/0133–25/0158; A61M 2025/015; A61M 2025/0161; A61M 2025/0163; A61B 2017/003; A61B 2017/00305; A61B 2017/00318; A61B 2019/2211; A61B 2019/2242; A61B 2019/2246; A61B 2019/2269; A61B 2019/2273; A61B 2019/2276
USPC .......................................... 600/585
See application file for complete search history.

(56) References Cited

U.S. PATENT DOCUMENTS

| | | |
|---|---|---|
| 2,057,952 A | 10/1936 | Schleimann |
| 3,091,235 A | 5/1963 | Richards |
| 3,773,034 A | 11/1973 | Burns et al. |
| 4,290,421 A | 9/1981 | Siegmund |
| 4,469,347 A | 9/1984 | Gier |
| 4,719,924 A | 1/1988 | Crittenden et al. |
| 4,753,223 A | 6/1988 | Bremer |
| 4,790,624 A | 12/1988 | Van Hoye et al. |
| 4,802,545 A | 2/1989 | Nystuen et al. |
| 4,838,859 A | 6/1989 | Srassmann |

(Continued)

FOREIGN PATENT DOCUMENTS

| | | |
|---|---|---|
| EP | 0254701 | 1/1988 |
| EP | 0315371 | 5/1989 |

(Continued)

*Primary Examiner* — Adam J Eiseman
(74) *Attorney, Agent, or Firm* — Baker & Hostetler LLP

(57) ABSTRACT

A surgical system can include a surgical probe having a deflectable tip, and a plurality of guide arms that are movable so as to cause the tip to deflect. Thus, the surgical probe can be steered toward a target anatomical location. The surgical system can further include a control system that includes a free floating user interface, and a motion sensor that detects motion of the user interface. The control system is configured to cause the probe tip to deflect in response to the detected motion of the user interface.

17 Claims, 12 Drawing Sheets

(56) References Cited

U.S. PATENT DOCUMENTS

| | | |
|---|---|---|
| 4,846,573 A | 7/1989 | Taylor et al. |
| 4,906,230 A | 3/1990 | Maloney et al. |
| 5,010,876 A | 4/1991 | Henley et al. |
| 5,054,501 A | 10/1991 | Chuttani et al. |
| 5,090,956 A | 2/1992 | McCoy |
| 5,128,671 A | 7/1992 | Thomas, Jr. |
| 5,188,111 A | 2/1993 | Yates et al. |
| 5,211,183 A | 5/1993 | Wilson |
| 5,238,005 A | 8/1993 | Imran |
| 5,331,948 A | 7/1994 | Utsumi et al. |
| 5,383,923 A | 1/1995 | Webster, Jr. |
| 5,395,328 A | 3/1995 | Ockuly et al. |
| 5,415,633 A | 5/1995 | Lazarus et al. |
| 5,480,382 A | 1/1996 | Hammerslag et al. |
| 5,507,725 A | 4/1996 | Savage et al. |
| 5,520,644 A | 5/1996 | Imran |
| 5,531,685 A | 7/1996 | Hemmer et al. |
| 5,588,964 A | 12/1996 | Imran et al. |
| 5,656,029 A | 8/1997 | Imran et al. |
| 5,704,898 A | 1/1998 | Kokish |
| 5,715,817 A | 2/1998 | Stevens-Wright et al. |
| 5,782,899 A | 7/1998 | Imran |
| 5,846,183 A | 12/1998 | Chilcoat |
| 6,048,329 A | 4/2000 | Thompson et al. |
| 6,123,699 A | 9/2000 | Webster, Jr. |
| 6,261,226 B1 | 7/2001 | McKenna et al. |
| 6,545,661 B1 | 4/2003 | Goschy et al. |
| 6,572,536 B1 | 6/2003 | Bon et al. |
| 6,592,520 B1 | 7/2003 | Peszynski et al. |
| 7,037,290 B2 | 5/2006 | Gardeski et al. |
| 7,081,090 B2 | 7/2006 | Strong et al. |
| 7,377,906 B2 | 5/2008 | Selkee |
| 7,449,002 B1 | 11/2008 | Wenstad |
| 7,662,091 B2 | 2/2010 | Bagley et al. |
| 7,974,681 B2 | 7/2011 | Wallace et al. |
| 8,251,977 B2 | 8/2012 | Partlett |
| 8,337,455 B2 | 12/2012 | Boulais |
| 8,343,096 B2 | 1/2013 | Kirschenman et al. |
| 8,430,621 B2 | 4/2013 | Jantti |
| 8,454,587 B2 | 6/2013 | Lalonde et al. |
| 8,465,442 B2 | 6/2013 | Freed |
| 8,467,853 B2 | 6/2013 | Hunter et al. |
| 8,475,436 B1 | 7/2013 | Jordan |
| 8,486,009 B2 | 7/2013 | Shih |
| 8,504,136 B1 | 8/2013 | Sun et al. |
| 8,681,101 B1 | 3/2014 | Haney et al. |
| 8,690,821 B2 | 4/2014 | Kirschenman et al. |
| 8,696,620 B2 | 4/2014 | Tegg |
| 8,734,312 B2 | 5/2014 | Conner et al. |
| 8,734,699 B2 | 5/2014 | Heidman et al. |
| 8,827,949 B2 | 9/2014 | Boulais |
| 2002/0177789 A1 | 11/2002 | Ferry et al. |
| 2004/0059191 A1 | 3/2004 | Krupa et al. |
| 2004/0259591 A1 | 12/2004 | Grams et al. |
| 2005/0131279 A1 | 6/2005 | Boulais et al. |
| 2005/0206612 A1 | 9/2005 | Teng |
| 2006/0111618 A1 | 5/2006 | Couvillon, Jr. |
| 2007/0156133 A1 | 7/2007 | McDaniel et al. |
| 2007/0242042 A1 | 10/2007 | Kelly |
| 2008/0091169 A1 | 4/2008 | Heideman |
| 2008/0108869 A1 | 5/2008 | Sanders et al. |
| 2010/0010437 A1 | 1/2010 | Miles et al. |
| 2010/0019153 A1 | 1/2010 | Zalameda et al. |
| 2012/0029334 A1 | 2/2012 | Tegg |
| 2012/0226103 A1 | 9/2012 | Gunday et al. |
| 2013/0002895 A1 | 1/2013 | McClung |
| 2013/0018307 A1 | 1/2013 | Lee et al. |
| 2013/0204138 A1 | 8/2013 | Belohlavek et al. |
| 2013/0253469 A1 | 9/2013 | Freed |
| 2014/0081290 A1 | 3/2014 | Hauck |
| 2014/0231590 A1 | 8/2014 | Trowbridge et al. |
| 2014/0246477 A1 | 9/2014 | Koch et al. |
| 2014/0257130 A1 | 9/2014 | Cao et al. |
| 2014/0263552 A1 | 9/2014 | Hall et al. |
| 2014/0276934 A1 | 9/2014 | Balaji et al. |
| 2014/0309666 A1 | 10/2014 | Shelton, IV et al. |

FOREIGN PATENT DOCUMENTS

| | | |
|---|---|---|
| EP | 0585321 | 3/1994 |
| EP | 0761250 | 3/1997 |
| EP | 1607119 | 12/2005 |
| EP | 1922991 | 5/2008 |
| EP | 2117636 | 11/2009 |
| EP | 2752218 | 7/2014 |
| WO | WO 92/19148 | 11/1992 |
| WO | WO 98/07001 | 2/1998 |
| WO | WO 2006/083306 | 8/2006 |
| WO | WO 2008/115665 | 9/2008 |
| WO | WO 2014/074986 | 5/2014 |

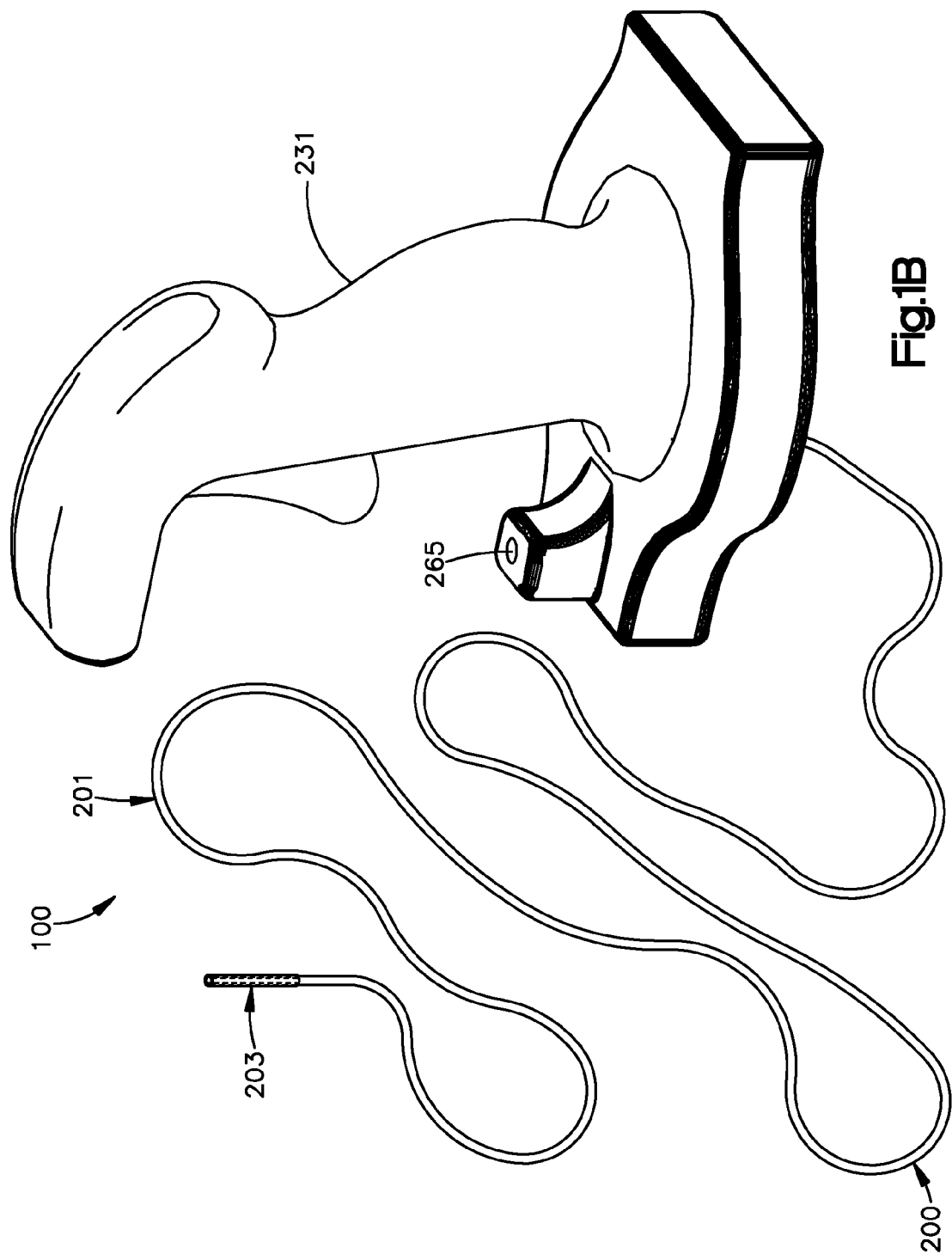

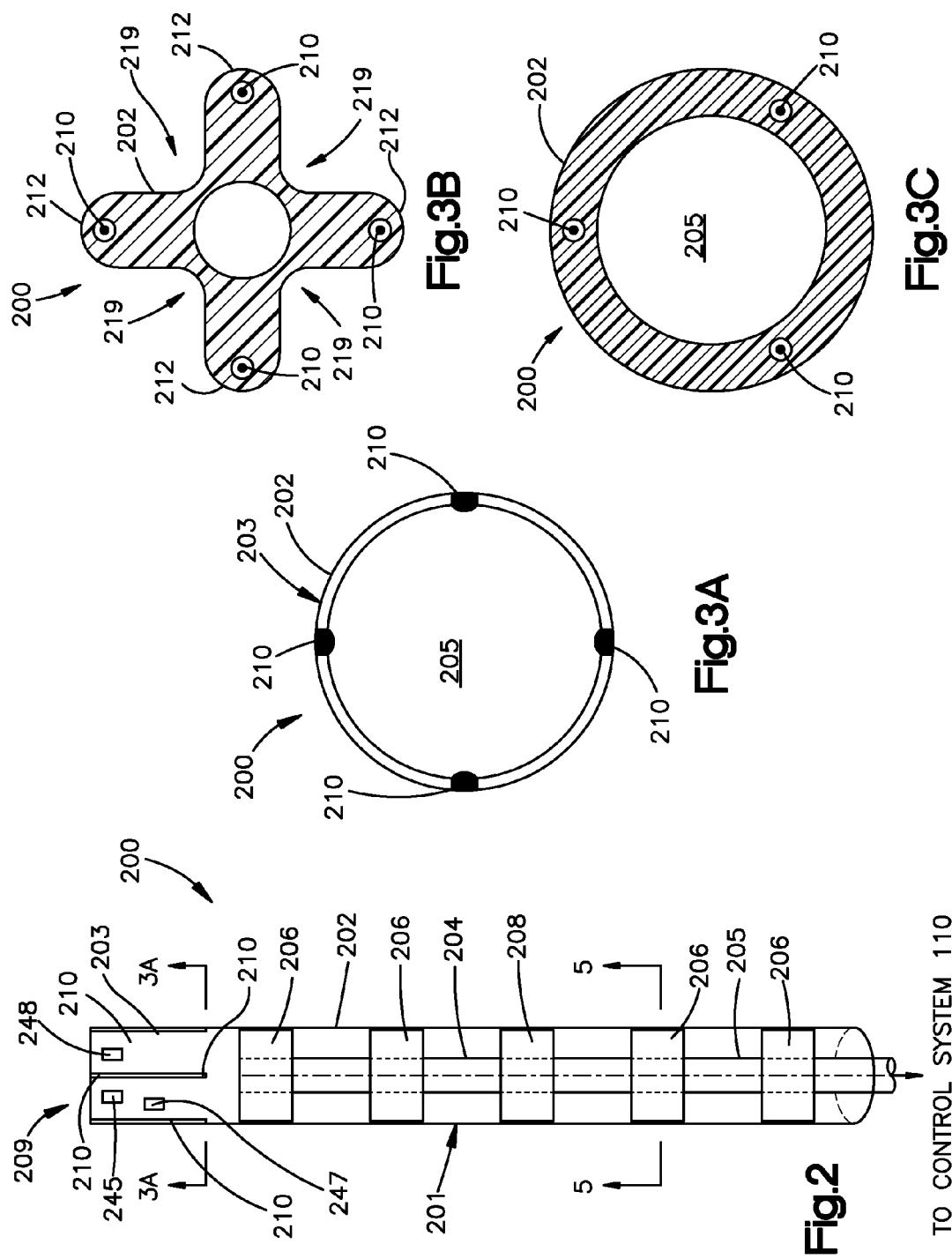

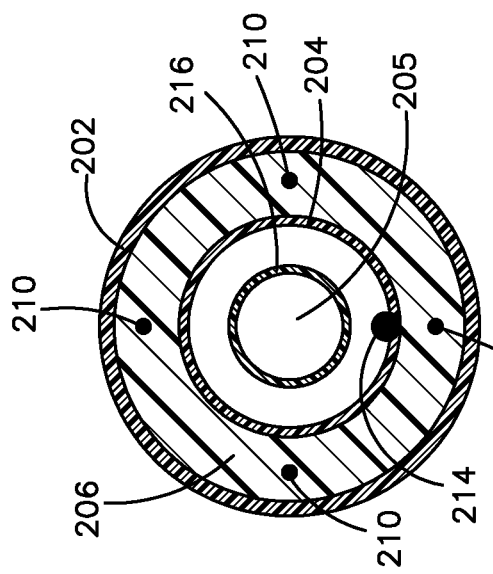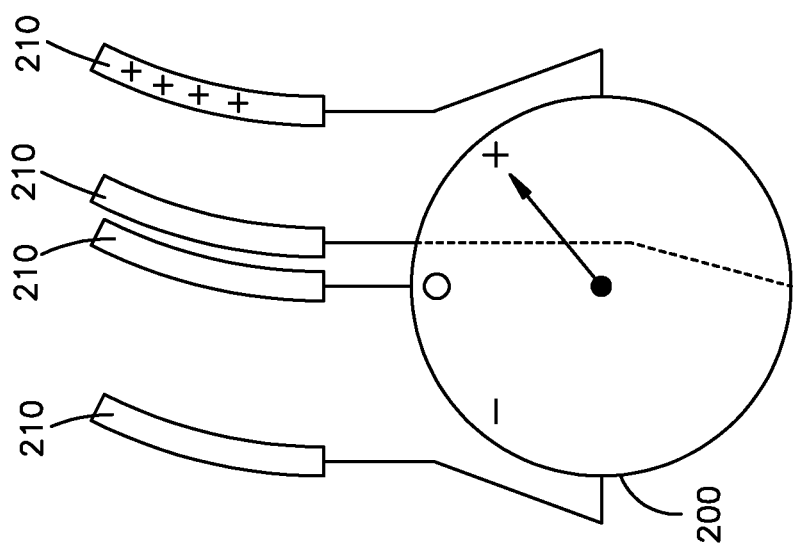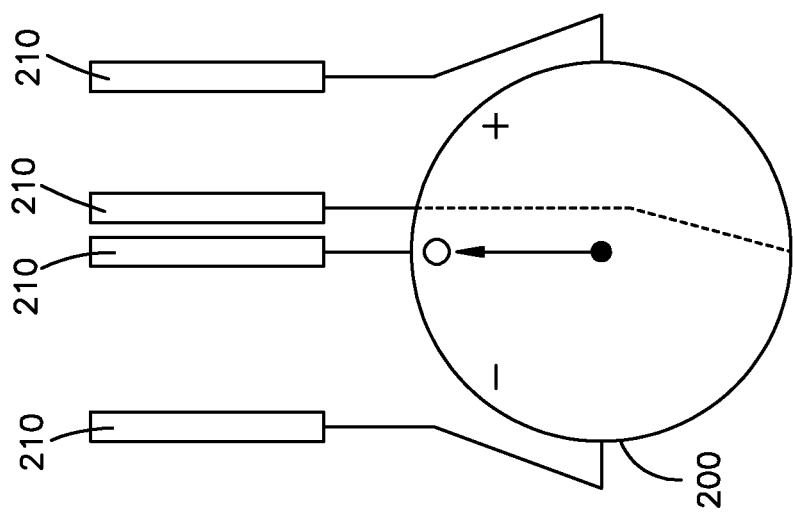

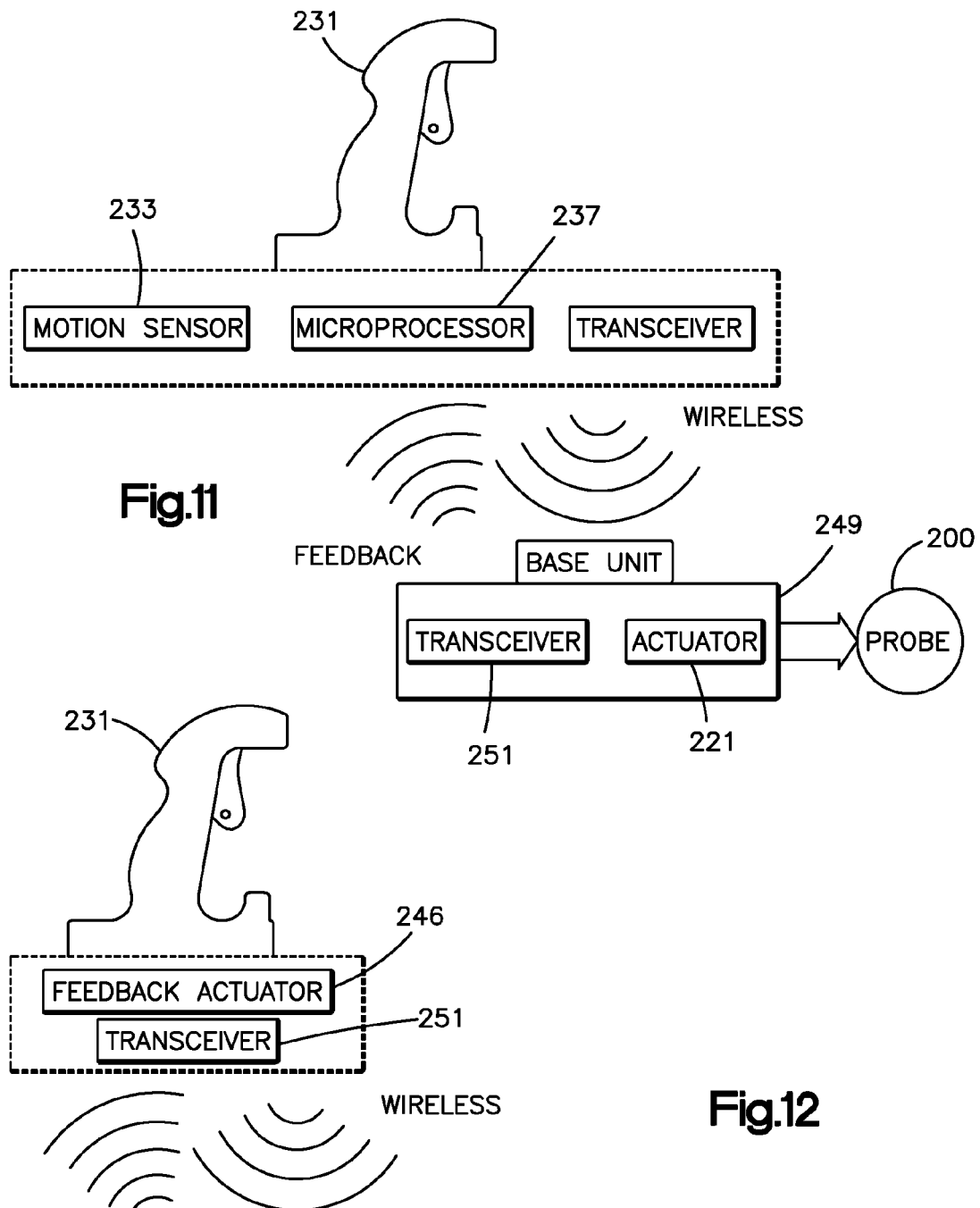

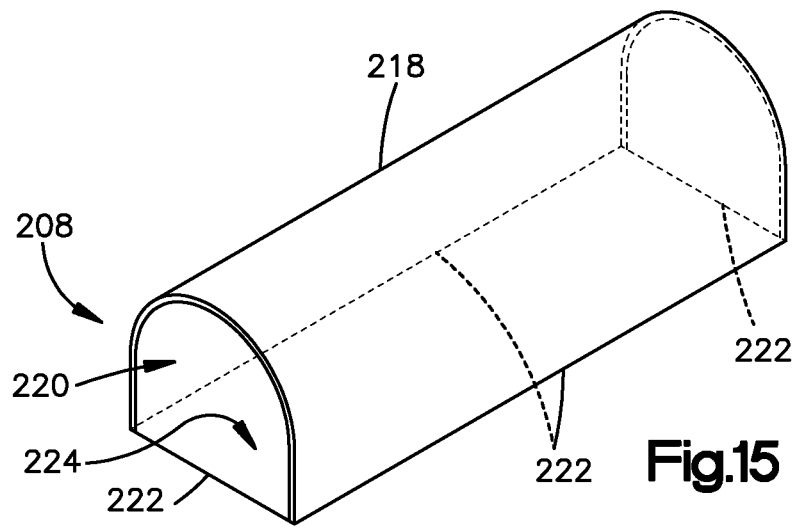
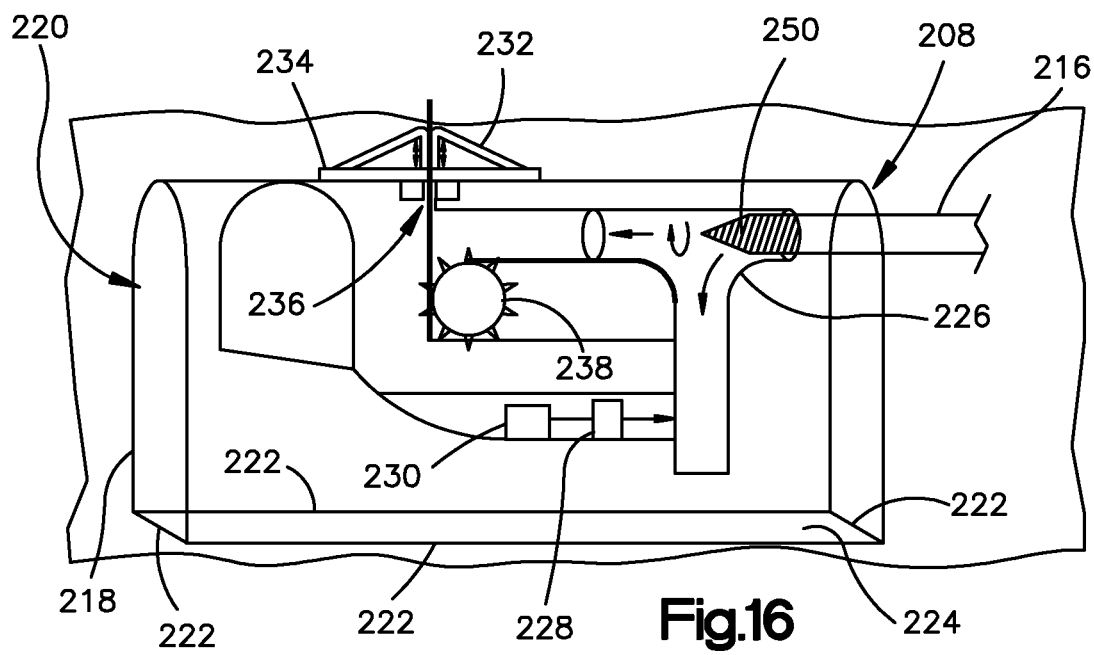
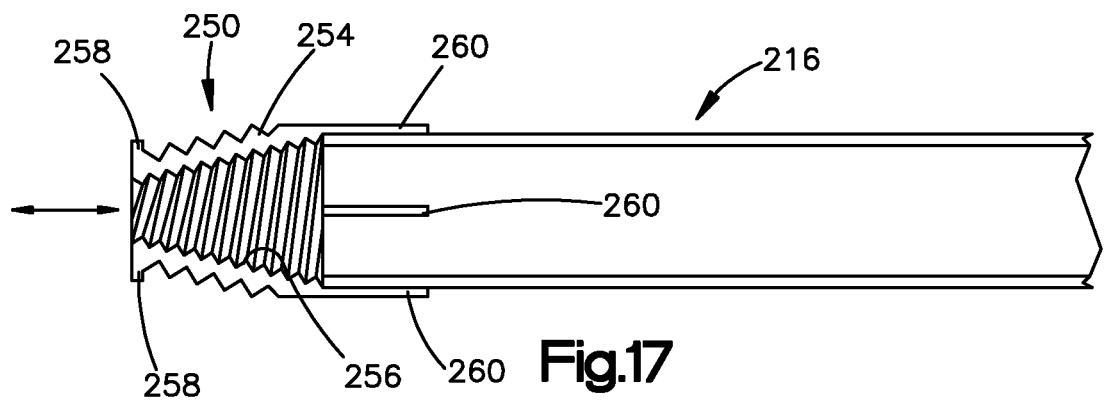

SURGICAL SYSTEM AND RELATED METHODS

CROSS-REFERENCE TO RELATED APPLICATIONS

This claims priority to U.S. Patent Application Ser. No. 61/918,846 filed Dec. 20, 2013, the disclosure of which is hereby incorporated by reference as if set forth in its entirety herein.

FIELD OF THE DISCLOSURE

The present disclosure relates to the field of surgical devices, and in particular relates to surgical access members.

BACKGROUND

Many parts of the body are inaccessible unless risky and highly invasive surgery is performed. Other bodily regions are reachable via vascular, digestive, reproductive, or other biological lumens, but are inaccessible to interventional methods due to biological parameters and the state of current tooling. Other surgical sites can be accessed directly (i.e., not intravascularly), but it is desired to reliably position the surgical instrument at a specific orientation with respect to the target anatomical location in situations that make the use of conventional surgical tooling difficult.

Basic deflection systems came into practice to give physicians control of remote tubing and surgical tools for various vascular and non-vascular applications that are out of reach for hand based operations. Initial steering systems used pull wires to manipulate a given tubular structure and produce deflection of the elongated tube. Such a bend allowed for vessel navigation, and directional pointingly for a tool or procedure function. The pull wire system began as one wire for single plane deflection. With better deflectable tubing and smaller pull wires, more than one pull wire have been installed into systems to allow for two plane deflection, and in some cases multi-plane deflection. Given the size required by mechanical wires to achieve more than one or two planes of deflection, most multi plane systems have usually been limited to robotic systems, large medical devices, and a large number of non-medical cameras and deflectable tubing primarily in the aerospace and industrial engineering sectors. At the same time, most bi-direction and omnidirectional (4 way) systems have relied on rotation along the central axis to torque steer the fixed deflection planes into new positions, which requires overcoming the resistance of tissues in contact with the length of deployed tubing.

Non-medical ceramics and materials research grew on a nearly adjacent timeline. Piezoelectric ceramics were visualized as alternate actuators to deflect medical tubing. Their application was limited by the degree of deflection allowed by their relatively high young's modulus. A similar alternative actuator, most notably Nitinol based materials, were used to replace mechanical pull wires as they were subsequently developed for other structural medical devices. However, Nitinol based deflection systems are not optimal due to their high temperature output and other factors.

SUMMARY

In accordance with one aspect of the present disclosure, a surgical system can include a surgical probe having a probe body and a probe tip that extends from the probe body in a distal direction. The surgical probe is elongate along a central axis. The surgical probe can include an outer annulus and a plurality of guide arms that are attached to the probe tip and disposed about the central axis. The surgical probe is configured to carry a surgical device. The surgical system can further include a control system that includes a free floating user interface, a motion sensor that detects motion of the user interface and generates motion signals in response to the detected motion, a processor that receives the motion signals from the motion sensor, and a plurality of actuators each in communication with the processor and coupled to at least one of the guide arms. The processor, in response to the motion signals, can apply deflection signals to at least one of the actuators that causes the at least one of the actuators to urge at least a portion of at least one of the guide arms to move in a proximal direction opposite the distal direction, which in turn applies a biasing force to the probe tip to deflect in a respective direction in which the at least one of the guide arms is spaced from the central axis.

DESCRIPTION OF THE DRAWINGS

The foregoing summary, as well as the following detailed description of an example embodiment of the application, will be better understood when read in conjunction with the appended drawings, in which there is shown in the drawings example embodiments for the purposes of illustration. It should be understood, however, that the application is not limited to the precise arrangements and instrumentalities shown. In the drawings:

FIG. 1B is a perspective view of a guidance component and a probe of the surgical system illustrated in FIG. 1A;

FIG. 2 is a schematic view of the probe illustrated in FIG. 1B;

FIG. 3A is a sectional side elevation view of the probe illustrated in FIG. 2, taken along line 3A-3A;

FIG. 3B is a sectional side elevation view of the probe similar to FIG. 3A, but having a geometry in accordance with an alternative embodiment;

FIG. 3C is a sectional side elevation view of the probe similar to FIG. 3A, but showing a different number of guide arms in accordance with another embodiment;

FIG. 4A is a schematic view of a plurality of guide arms of the probe, shown in a neutral or non-deflected state;

FIG. 4B is a schematic of the guide arms illustrated in FIG. 4A, shown in a deflected state;

FIG. 5 is a sectional side elevation view of the probe illustrated in FIG. 2, taken along line 5-5;

FIG. 11 is a schematic view of the guidance component similar to FIG. 10B, but constructed in accordance with an alternative embodiment;

FIG. 12 is a schematic view of the guidance component similar to FIG. 11, but constructed in accordance with an alternative embodiment;

FIG. 15 is a perspective view of the body of the surgical device embodiment;

FIG. 16 is a side cut away view of the surgical device embodiment illustrated in FIG. 15; and FIG. 17 is a side cross-section of the tip end of a surgical member of the surgical device embodiment illustrated in FIG. 16.

DETAILED DESCRIPTION

In the Summary and in the Detailed Description, reference is made to particular features, including method steps. Where a particular feature is disclosed in the context of a particular aspect or embodiment, that feature can also be used, to the extent possible, in combination with and/or in the context of other aspects and embodiments.

In this section, embodiments will be described more fully. These embodiments may, however, take many different forms and should not be construed as limited to those set forth herein.

The surgical system described here allows medical professionals to image and have surgical access to parts of the body that can be otherwise less accessible without performing major surgery or using other ineffective remote surgical tooling. The surgical system advantageously includes a probe that has a deflectable tip so as to access a target anatomical location. The probe can access the target anatomical location directly through an incision in the patient's skin, or can travel through an anatomical vessel, which can be a blood vessel, nonvascular tubular structures in the digestive system, reproductive system, or other anatomical vessels, or non-vascular lumen to access the target anatomical location. In instances where the probe travels endovascularly to the target anatomical location, the probe can be adapted to image and perform surgery from within the blood vessel. The term "blood vessel" as used herein refers to the part of the circulatory system that transports blood throughout the body and includes arteries, veins, and capillaries. The probe may be used to perform substantially minimally-invasive surgical procedures inside or outside the vessel in which the probe is located. Extravascular surgical procedures may include, for example, delivery of drugs, biopsies, cauterization, scar tissue removal, tumor removal, tissue repair, tissue reconstruction, suction of internal bleeding, electrical stimulation, and emergency trauma care among others.

Figure 1A:
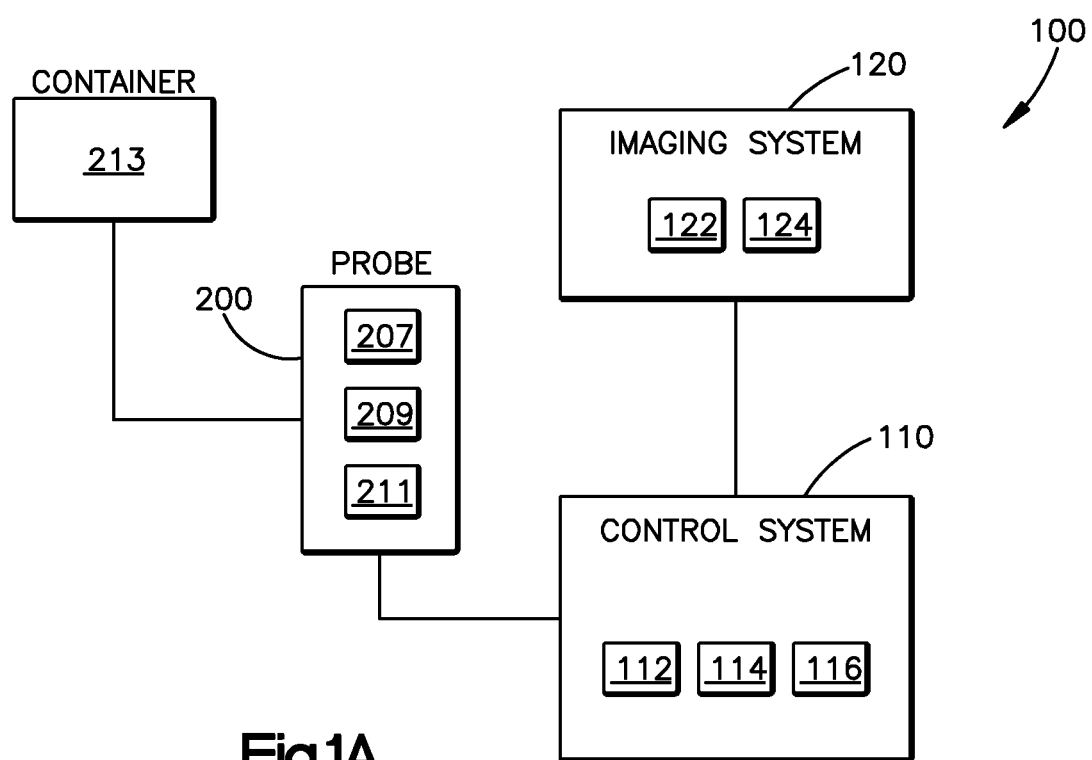
FIG. 1A is a block diagram of a surgical system constructed in accordance with one embodiment.

Referring to FIGS. 1A-1B, a surgical system 100 can include a control system 110, an imaging system 120, and a surgical probe 200. The control system 110 can be in data communication with both the imaging system 120 and the probe 200. The probe 200 includes a guidance component 209, and the control system 110 includes a guidance component 114 that is configured to control the guidance component 209. The guidance component 209 is adapted to assist the user so as to position a tip of the probe at a desired position and/or orientation with respect to a target anatomical location. The probe 200 is further configured to carry a surgical component 207. The surgical component 207 is adapted to perform a surgical procedure on the target anatomical location. When the probe 200 is endovascular, the surgical procedure may be executed within the vessel itself or outside the vessel by opening the vessel wall. The probe 200 can further include an imaging component 211. The imaging component 211 allows the surgical system 100 to image the section of the body in which the surgical component 207 is located so that the surgeon can visualize that section of the body both during travel to the target anatomical site, and during the surgical procedure of the target anatomical site. It should also be appreciated in some instances that the probe 200 does not carry a surgical component 207, for instance when the probe 200 is being used to gain visualization of the target anatomical site for diagnostic purposes.

The probe 200 is adapted to be inserted through an incision of the skin, and is configured to be inserted to a target anatomical location. The probe 200 can be configured to access the target anatomical location directly through the cavity of a patient's body. As will be appreciated from the description below, the probe 200 has a probe body 201 and a distal probe tip 203 that extends in a distal direction from the probe body 201. The distal probe tip 203 defines the leading end of the probe 200 as it navigates in the anatomy toward the target anatomical location. The distal probe tip 203 can be omnidirectionally deflectable with respect to the probe body 201. Accordingly, when the distal probe tip 203 is disposed adjacent the target anatomical location, and the surgeon wishes to place the distal probe tip 203 at a desired orientation with respect to the target anatomical location, the surgeon can cause the distal probe tip 203 to deflect with respect to the probe body 201 to a desired position. For instance, in some embodiments, the imaging component 211 can include a camera, and the surgeon can deflect the distal probe tip 203 such that the camera provides visual access to the target surgical location. Further, deflection of the probe tip 203 can allow the surgical component 207 to access the target anatomical location in a desired manner. In other embodiments, the probe 200 can travel through a blood vessel to the target anatomical location. When the probe 200 is placed inside a blood vessel and travels endovascularly to the target anatomical location, the distal probe tip 203 can be deflected in order to allow the probe 200 to navigate the bends and curves of the vasculature or any other biological lumen. In this regard, it should be appreciated that the imaging component 211 may also be used to image ahead of the probe 200 to aid with determining where the probe should be positioned and when and how the distal probe tip 203 is to be deflected.

Referring now to FIGS. 2-5 additional details of the endovascular probe 200 are shown. The probe 200 is elongate along a central axis, and includes an outer hollow annulus 202 made of a flexible material. For example, the flexible material can be a silicone or plastic based biocompatible material or the like. The annulus 202 forms a cylindrical envelope around other components of the probe 200. When the probe is to be used endovascularly, the annulus 202 can have an outer cross-sectional dimension, such as a diameter, that is small enough to fit within a blood vessel. In this regard, it is recognized that probe size is an issue in a non vascular setting just to for fit within the biological lumen. Probe size is also an issue in a vascular setting in regards to perfusion. An occluding object within any blood vessel can quickly become a dangerous hazard to the organism. Blood flow is responsible for nutrients transport, transfer of other compounds, and gas exchange and a break in this flow can results in localized tissue damage with longer durations causing system wide problems and/or death. Thus, it is desired that any intravascular probe is small enough to allow for perfusion. Greater interior tooling room of the probe 200, and smaller overall tubing size with more efficient actuation systems allows deflectable medical devices to reach smaller target anatomical locations and normally accessible anatomical locations with less risk. Accordingly, the diameter of the probe 200 may vary depending on the size of the vessel (e.g., vasculature or non-vasculature lumen) into which it is to be inserted. By way of example, the outer probe diameter may be less than 1 mm (3 French), 1 mm to 4 mm (4-12 French), or 4.333 mm and 6.333 mm (13 French to 19 French), and 6.667 mm and above (20 French and greater). The probe 200 can further include a tubular member 204 that extends substantially along the longitudinal axis of the probe 200 and through the annulus 202. The tubular member 204 can further extend to the control system 110. The tubular member 204 may include a thin layer of metal in a wire-like braid configuration such as stainless steel to provide some rigidity to the probe 200 while allowing the probe 200 to be flexible. The tubular member 204 defines a central axis that can define the central axis of the probe 200. It should be appreciated that the central axis can be straight or curved, and can change in geometry as the probe 200 changes in geometry. Thus, the tubular member 204 can define a central lumen 205 of the probe 200. Alternatively, part or all of the probe 200 can be devoid of the tubular member 204, such that the annulus 202 defines the central lumen 205 of the probe 200. For instance, instead of the tubular member 204, the probe 200 can include a woven metal that extends along at least a portion of the length of the annulus 202. The woven metal can, for instance, be a stainless steel or any suitable alternative stiffener. The stiffener can extend along the probe body 201, and can terminate at the interface between the probe body 201 and the probe tip 203.

The guidance component 209 can include a plurality of guide arms 210 that are each positioned at a location radially offset from the central axis of the probe 200 along a respective direction. For instance, the guide arms 210 can be disposed on a peripheral side of the probe 200. In one example, the guide arms 210 can extend longitudinally through the annulus 202. Each of the guide arms 210 can be secured to the distal probe tip 203. For instance, the guide arms 210 can each have a distal end that is attached directly to the distal probe tip 203, or can be attached to an intermediate structure that, in turn, is attached to the distal probe tip 203. At least a portion of each of the guide arms 210 can be movable in a proximal direction that is opposite the distal direction. Thus the proximal direction is away from the probe tip 203. Because each of the guide arms 210 is secured to the probe tip 203, movement of the guide arm 210 in the proximal direction applies a force to the probe tip 203 in the respective direction defined by the direction from the central axis of the probe 200 to the guide arm 210. The applied force to the probe tip 203 biases the probe tip to deflect in the respective direction.

The guide arms 210 can be spaced circumferentially equidistantly about the central axis of the probe 200, or can be variably spaced as desired. It is recognized that selective movement of a predetermined one or more of the guide arms 210 in the proximal direction can result in deflection of the probe tip 203 in any direction as desired within an omnidirectional range of directions, such as any direction within a 360 degree range of motion from the central axis where any angle of ben curvature from 0 to 180 degrees or more can be formed along any of these divergent directions. For instance, movement of first and second ones of the guide arms 210 can produce a vectored composite deflection of the probe tip 203 that is a combination of the first and second respective directions. The amount that the first and second of the first and second respective directions contribute to the vectored composite deflection can depend on the amount of movement of the first one of the guide arms 210 relative to the second one of the guide arms 210. It should be appreciated, of course, that the probe 200 can include any number of guide arms 210 as desired, such as three or more. When the probe 200 includes four guide arms 210 each spaced at ninety degrees from each other as illustrated in FIG. 3A, it is recognized that the guide arms 210 can be divided into two pairs of opposed guide arms 210 that are spaced 180 degrees from each other, and are thus opposite each other through the central axis of the probe 200. It should be appreciated that at least three guide arms 210 positioned about the central axis of the probe 200 can allow for omnidirectional deflection of the probe tip 203 as desired, as illustrated in FIG. 3C.

Referring now to FIG. 3B, while the annulus 202 can be tubular with a substantially circumference as illustrated in FIGS. 3A and 3C, it should be appreciated that the annulus 202 can define any geometry as desired. For instance, the annulus 202 can define a plurality of nodes 212 that each surround a respective one of the guide arms 210 and project radially outward with respect to the central axis of the probe 200. The annulus 202 can define respective recesses 219 that extend between adjacent ones of the nodes 212. Accordingly, when the probe 200 is disposed in a blood vessel, the recesses allow for perfusion through the recesses 219.

With continuing reference to FIGS. 1-5, the annulus 202 can be a thermoset or thermoplastic material that can be flexible, yet stiff enough to return to a normal resting positional along its longitudinal access. The annulus 202 can be a pure material (silicone, Pebax derived, or the like), a blend with stainless steel braids, or a stainless steel or similar braiding, and a system of lumens that are coated in a biocompatible material such as silicone or pebax. The annulus 202 can have a durometer change at an interface between the probe body 201 and the probe tip 203, such that the probe body 201 has a higher durometer than the probe tip 203. The interface can be disposed at a location at about the distal end of the annulus 202, such that the probe tip 203 comprises a 4 inch segment or less length of the distal end of the annulus. The change in the tubing material durometer (and possibly the stainless steel braid configuration) creates a mechanical stopping location with respect to deflection. Thus, the high durometer setting crosses over into a low durometer setting at the interface, such that the stiffer proximal length of the annulus 202 provides a stiffer probe body 201, thereby isolating deflection to the more flexible probe tip 203 in response to movement of the guide arms 210. This change in stiffness can also be accomplished with a metallic braid system that complements the durometer change in the material.

Figure 6:
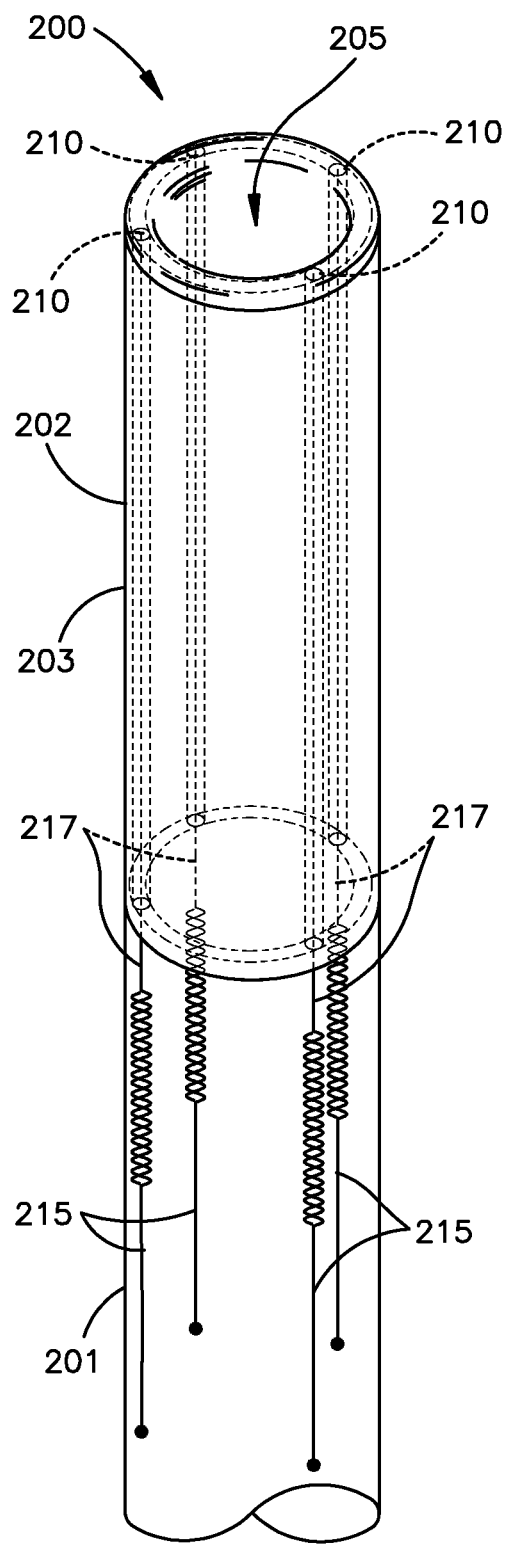
FIG. 6 is a perspective view of the probe illustrated in FIG. 1B, with portions shown transparent to illustrate internal components of the probe.
Figure 7:
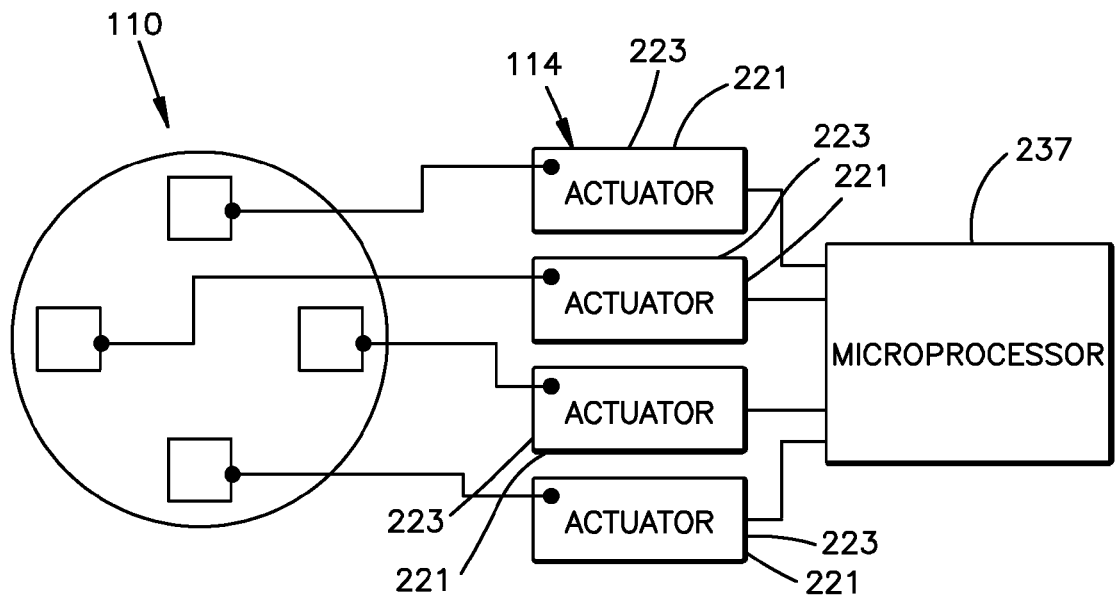
FIG. 7 is a schematic illustration showing a plurality of actuators of a control system in electrical communication with the guide arms of the probe illustrated in FIG. 6.

Referring now to FIGS. 6-7, the guidance component 114 of the control system 110 can include a plurality of actuators 221 that are in communication with the guidance component 209 so as to control deflection of the probe tip 203. For instance, each of the actuators 221 can be configured to control movement of at least one of the guide arms 210. In one embodiment, at least a portion of each of the guide arms 210 can be made of a shape memory material that contracts along its length in in response to an applied electric current, but returns to its original shape when the current is removed. In this embodiment, the actuators 221 can be configured as current flow regulators 223 that are in electrical communication with respective different ones of the guide arms 210, and are configured to selectively supply electrical current to the respective ones of the guide arms 210. For instance, the current flow regulators 223 can be configured as variable resistor. When no electrical current is supplied to the guide arms 210 (FIG. 4A), each of the guide arms 210 extends substantially straight. In contrast, when electrical current is supplied to one or more of the guide arms 210 (FIG. 4B), the one or more of the guide arms 210 contracts along its length, which causes all of the guide arms 210 to extend along its length as it bends in substantially the same direction as the deflection of the probe tip 203 in response to the contraction of the at least one of the guide arms 210. When the electrical current is subsequently discontinued to the one of the guide arms 210, the guide arms 210 revert to their original substantially straight configuration. As described above, by electrically stimulating various ones of the guide arms 210 in various combinations, unique angles of probe tip deflection can be created within an omnidirectional range of angles as desired. As will be appreciated from the description below, movement of the user interface can control the direction and amount of tip deflection.

As described above, at least a portion of each of the guide arms 210 can be made from a shape memory material 215. The shape memory material can be a nickel-titanium derived alloys, commonly known as Nitinol. In particular, the shape memory material can be a low transition temperature (e.g., less than 100 Celsius, such as approximately 60 Celsius or higher) Nitinol material, commercially available from Memry (a SAES group company), having a place of business in Milan, Italy. A first portion of each of the guide arms 210 can include an electrical conductor 217, and a second portion of each of the guide arms can include the shape memory material 215 that is in electrical communication with the electrical conductor 217. The electrical conductor 217 can be interwoven with the shape memory material 215 to thereby form a looped weave or any suitable alternative configuration that maintains reliable contact between the electrical conductor 217 and the shape memory material 215 and allows a tight connection between the later to prevent the shape memory material 215 to move its entangled fixed end during actuation. The weave can be disposed in the outer annulus 202 or otherwise embedded in an electrical insulator. The shape memory material 215 and the electrical conductor 217 can both be configured as a wire in one embodiment.

In one example, the shape memory material 215 can be attached to the probe tip 203 at one end, and the electrical conductor 217 at its other end, such that electrical current applied to the electrical conductor 217 from the current flow regulator 223 travels to the shape memory material 215, thereby causing the shape memory material to contract as described above. It is appreciated that higher levels of electrical current and higher durations of this current cause higher levels of contraction of the shape memory material 215. Alternatively, a first end of the shape memory material 215 can be attached to a first electrical conductor 217, which in turn is attached to the probe tip 203, and a second end of the shape memory material 215 can be attached to a second electrical conductor 217. The second electrical conductor 217 can receive the electrical current from the current flow regulator 223, and communicates the electrical current to the shape memory material 215, which contracts along its length as described above. Alternatively still, the shape memory material 215 can be disposed at the proximal end of the probe 200, and a pull wire can extend from the shape memory material 215 to the probe tip 203. Thus, the shape memory material 215 can receive the electrical current from the current flow regulator, and in response can contract along its length. In all embodiments, the guide arm 210 is offset radially from the central axis of the probe 200 in a respective direction, such that contraction of the shape memory material 215 applies a force to the probe tip 203 that biases the probe tip 203 to deflect in the respective direction. It is appreciated that while one or more of the guide arms 210 contract so as to bias the probe tip to deflect, the others of the guide arms 210 resiliently expand along their length in order to allow the probe tip 203 to deflect.

Figure 8:
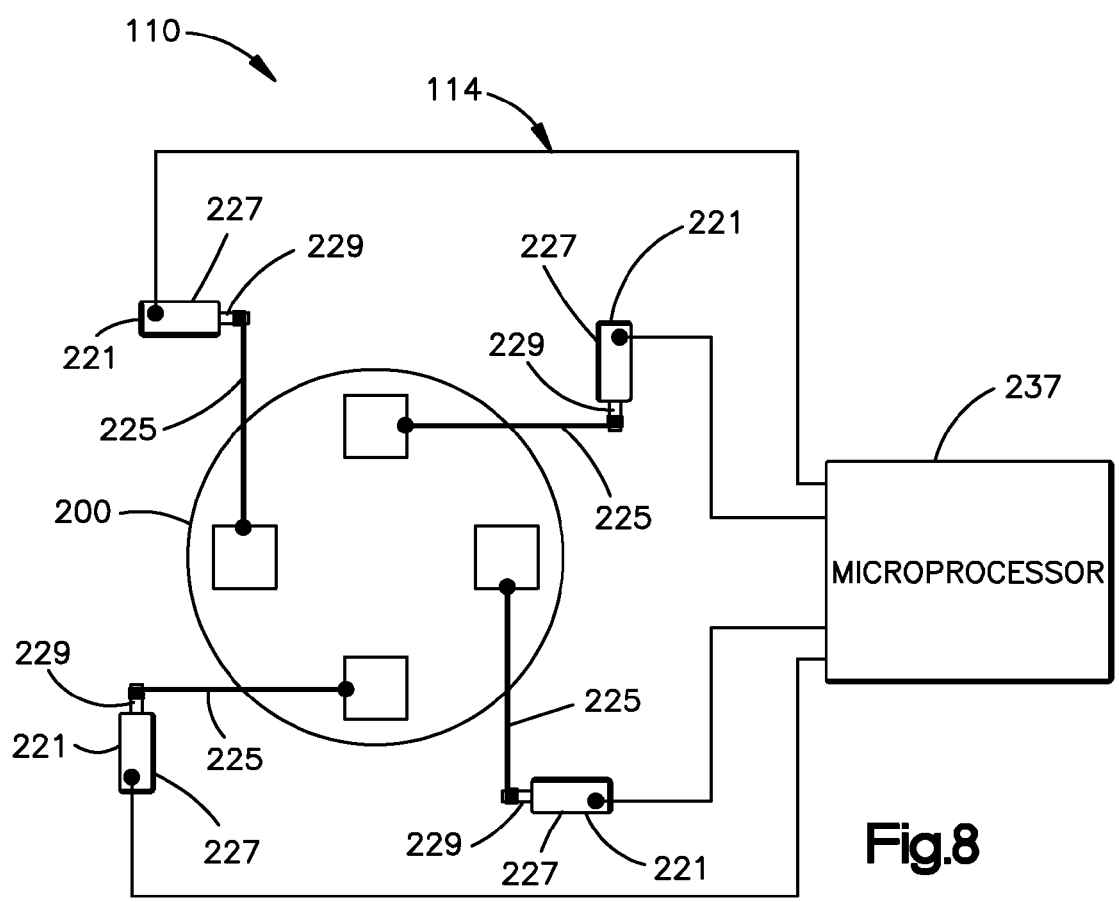
FIG. 8 is a schematic illustration showing a plurality of actuators of a control system in electrical communication with the guide arms of the probe in accordance with another embodiment.

Alternatively, referring now to FIG. 8, each of the guide arms 210 can be configured as pull wires 225. The pull wires 225 can be spaced from the central axis of the probe 200 along a respective direction, and can be secured to the probe tip 203 in the matter described above. Accordingly, when the pull wires move in the proximal direction, the pull wires 225 apply a force to the probe tip 203 that biases the probe tip 203 to deflect in the respective direction. In one embodiment, the actuators 221 can be configured as actuators that are configured to apply a physical force to the pull wires. For instance, the actuators 221 can be configured as servo motors 227 each having a movable servo arm 229 that is secured to at least one of the pull wires 225. In one example, each servo arm 229 is attached to a respective one of the pull wires 225. Accordingly, movement of the servo arm 229 in the proximal direction causes the pull wires 225 attached to the servo arm 229 to translate in the proximal direction, thereby biasing the probe tip 203 to deflect in the manner described above. It is appreciated that while one or more of the pull wires 225 move in the proximal direction, the others of the pull wires 225 move in the distal direction in order to allow the probe tip 203 to deflect. Thus, the servo arms 229 that do not move the respective pull wires 225 in the proximal direction can either passively allow the respective pull wires 225 to move in the distal direction, or can actively move the respective pull wires 225 in the distal direction.

Figure 9:
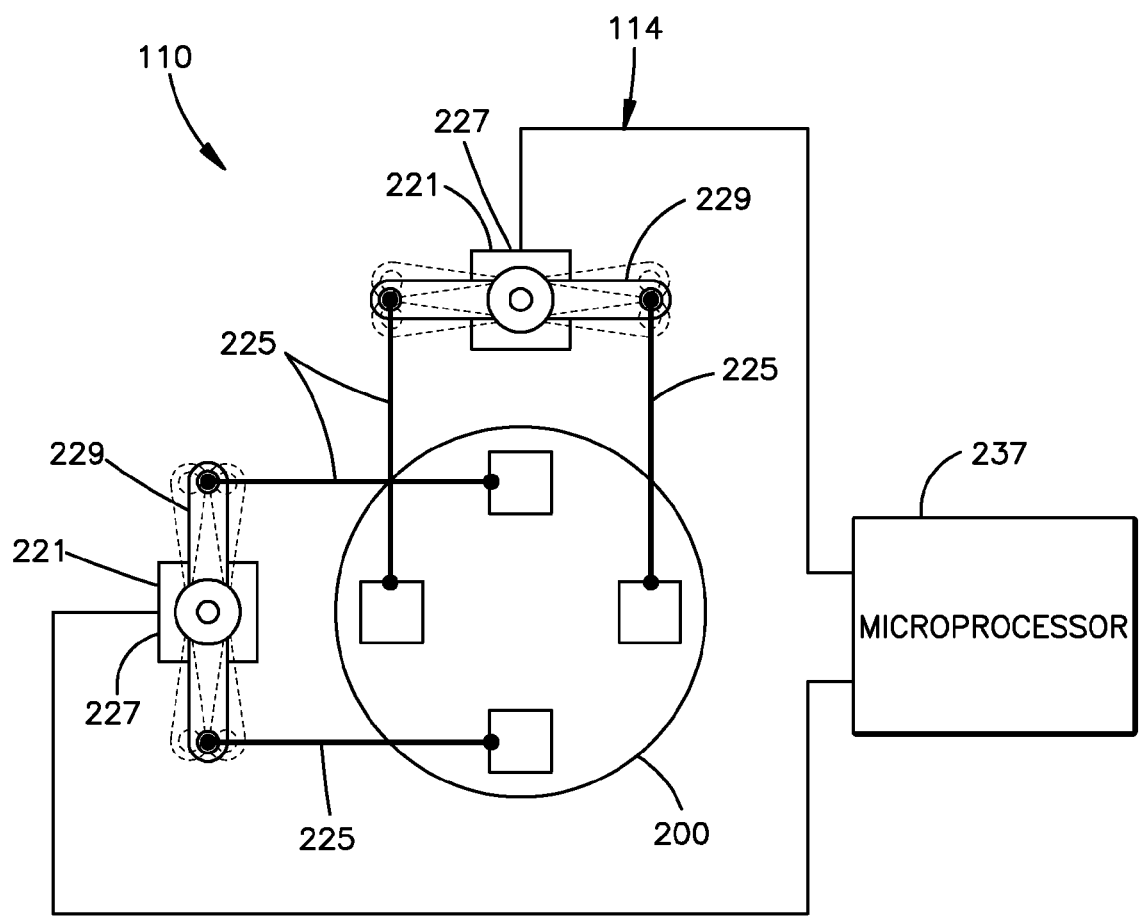
FIG. 9 is a schematic illustration showing a plurality of actuators of a control system in electrical communication with the guide arms of the probe in accordance with yet another embodiment.

Referring to FIG. 9, in another example, for instance where the probe includes pairs of pull wires 225 that are spaced from each other 180 degrees (e.g., through the central axis of the probe 200), each of the servo motors 227 can individually control a pair of the pull wires 225. While one wire of a pair of pull wires 225 is pulled in the proximal direction, the second wire of the same pair of pull wires 225 is pushed in the distal direction. In this regard, it is appreciated that rotation of the servo arm can cause a first end of the servo arm to move in the proximal direction, and a second end of the servo arm to move in the distal direction. Thus, when a first one of the pair of pull wires 225 is attached to the first end of the servo arm 229, and a second one of the same pair of pull wires 225 is attached to the second opposite end of the servo arm 229, movement of the servo arm causes the first one of the pair of pull wires 225 to move in the proximal direction, and causes the second one of the pair of pull wires 225 to move in the distal direction.

Thus, it will be appreciated in some instances that a guide arm offset 180 agrees from a pulling guide arm can be pushed in the distal direction to alleviate tension and further enhance deflection. This combination is made possible by having two guide arms attached to different ends of the same lever arm of a servo motor.

Referring now to FIGS. 1A-2 and 5, and as described above, the imaging component 211 can include at least one camera that provides visual access of anatomy that surrounds the probe 200. For instance, the imaging component 211 of the probe 200 can include at least one ultrasound transducer, such as a plurality of ultrasound transducers 206. The ultrasound transducers 206 can be spaced from each other along the length of the probe 200 about a surgical device 208 of the surgical component 207. The ultrasound transducers 206 are configured to communicate with the imaging controls 112 of the control system 110 via a communication line 214, such as wiring, fiberoptics, both, or the like, positioned in the tubular member 204. The communication line 214 may include more than one set of wires that are connected to different components. The transducers 206 independently transmit and receive an ultrasound signals into/from the body, which are then communicated to the imager 122. The imager 122 compiles the signals from each transducer 206. Because each transducer 206 is located in a different position, by compiling the signals together, the imager 122 is able to generate a three-dimensional ultrasound image that is shown on the display 124. This allows the user to have a substantially three-dimensional view of the section of the body on which the surgical procedure is to be performed, as well as a view of the surgical components and their activities. In this example, the transducers 206 are spaced about the surgical device 208 to provide an image of the body in the vicinity of the surgical device 208 so that the user can view the image dynamically during surgery on the display 124. The transducer adjacent the guide arms 210 may also be adapted to image ahead of the probe 200.

Alternatively or additionally, the probe 200 can be fluoroscopically imaged as it navigates toward the target anatomical location. For instance, at least a portion of the probe can be made of a radio-opaque material. Alternatively or additionally, the probe can include a plurality of radio-opaque markers that appear visible under fluoroscopic imaging. For instance, the probe 200 can include radio-opaque markers about its perimeter and at the probe tip 203.

Figure 10A:
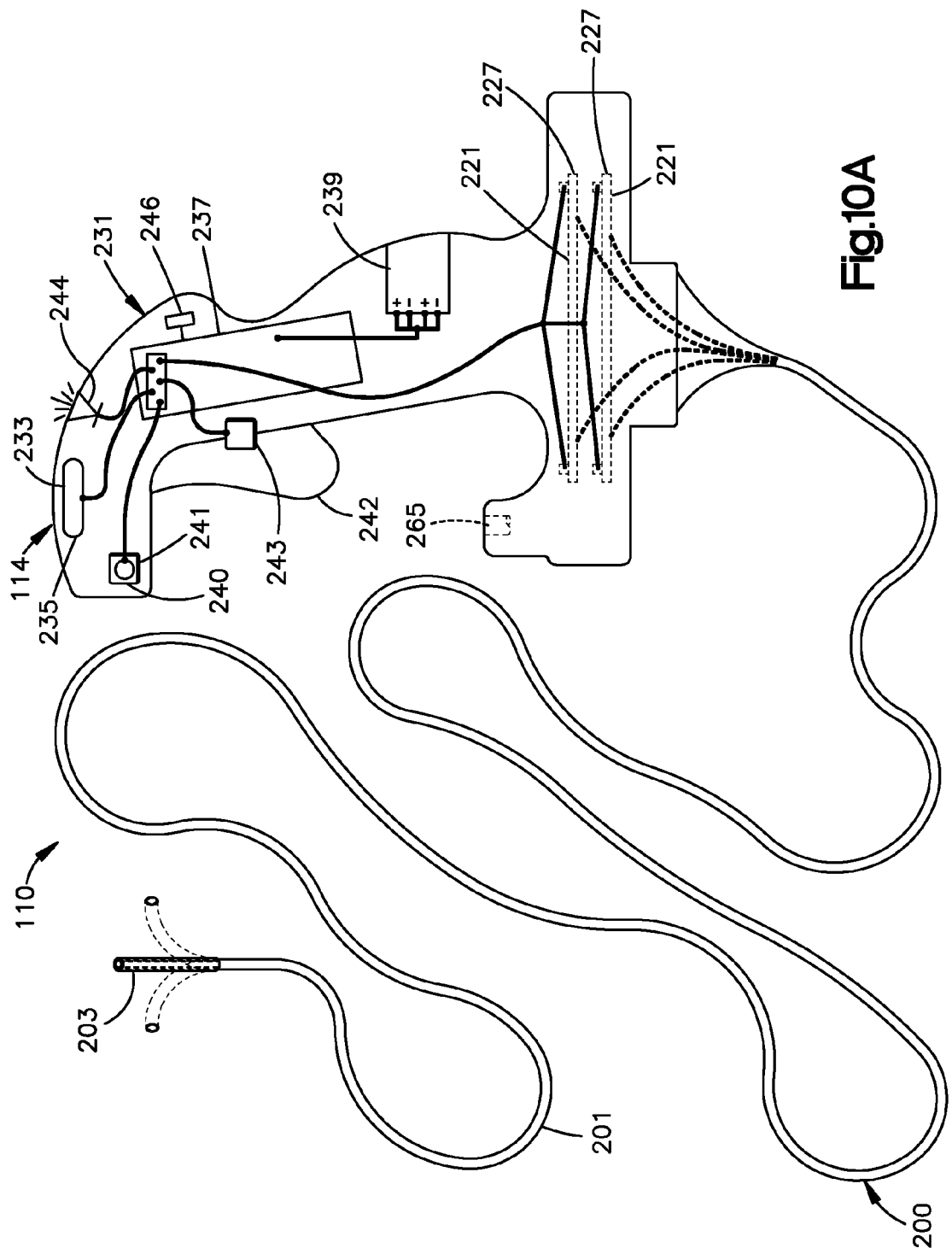
FIG. 10A is another perspective view of guidance component and the probe as illustrated in FIG. 1B, but further showing schematic illustrations of various components of the control system.
Figure 10B:
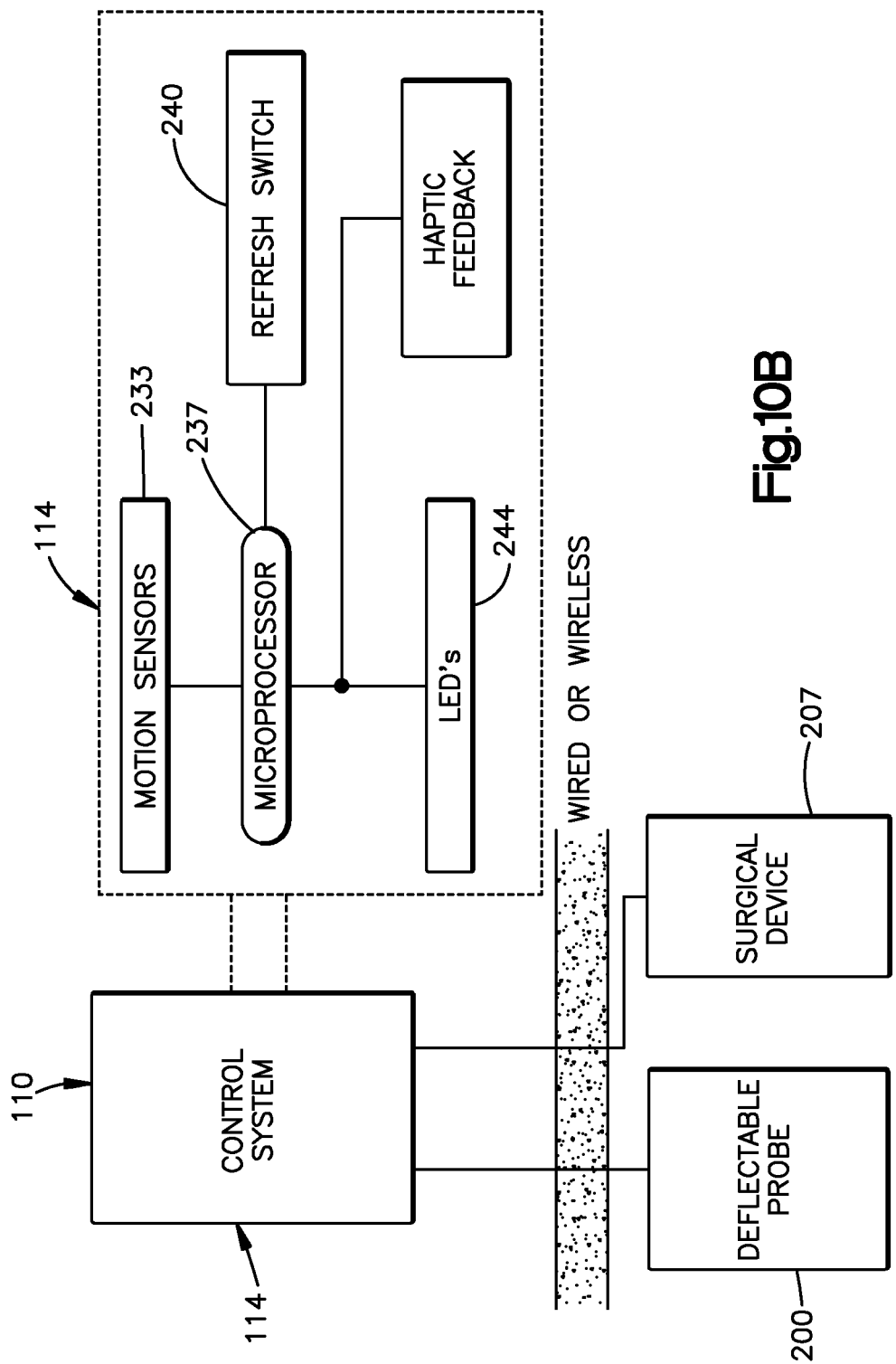
FIG. 10B is a schematic view of the guidance component illustrated in FIG. 10A.

Referring now to FIGS. 10A-10B, the control system 110 is configured to mechanically and/or electronically operate the various components of the probe 200 via input by a user. For instance, the control system 110 can include imaging controls 112 that communicate with the imaging system 120 and imaging component 211 to allow the user to generate the desired imaging parameters as described above. The imaging system 120 receives image information from the imaging component 211 to generate an image therefrom. The image may be shown on the imaging system display 124, which can be configured as a display screen such as a conventional computer monitor or television screen. Alternatively, the imaging controls 112 can be separate from the control system 110. The control system 110 can further include surgical controls 116 that are configured to communicate with the surgical component 207 carried by the probe 200 to allow the user to operate the functions of the surgical component 207. Alternatively, the surgical component 207 can be controlled by its own set of controls that are separate from the control system 110.

As described above, the guidance component 114 of the control system 110 is configured to communicate with the guidance component 209 of the probe 200 to guide the probe tip 203 to a desired position or orientation in the anatomy. For instance, the guidance component 114 can include a user interface 231, which can be free floating in all directions, including six degrees of freedom. In other words, the user interface 231 can be grasped by a user and freely manipulated in air without being supported by a support structure. Thus, the user interface 231 can be operated at any suitable location in the operating room as desired without constraint, thereby providing flexibility to the surgical work environment. The user interface 231 can have any suitable size and shape as desired, and can be ergonomically friendly so as to define a grip surface that is designed to fit the hand or fingers of the user so as to facilitate a secure grip.

The guidance component 114 can include at least one motion sensor 233 that is carried by the user interface 231. The motion sensor 233 can be configured as one or more three-dimensional accelerometers 235 or alternatively constructed motion sensors as desired. The guidance component 114 can further include a processor, which can be configured as a microprocessor 237, that is in communication with the at least one motion sensor 233. The at least one motion sensor 233 can be positioned proximate an outer perimeter of the user interface 231 such that the motion sensor 233 is sensitive to movement of the user interface 231. Accordingly, the at least one motion sensor 233 can generate motion signals, in response to movement of the user interface 231 from a neutral position, and transmit the motion signals to the microprocessor 237. The motion signals can indicate the direction of movement of the user interface 231 with respect to the neutral position, and also the amount of movement of the user interface 231. For instance, the user interface 231 can be moved (e.g., translated, angulated, or a combination thereof) to the left, to the right, up, down, and combinations thereof. The motion sensor senses the motion of the user interface from a neutral position, and generates motion signals that are received by the microprocessor 237.

The microprocessor 237, in turn, is configured to generate deflection signals that are received by at least one of the actuators 221. In response to the deflection signals, the at least one of the actuators 221 causes the guide arm 210 to move in the proximal direction, thereby causing the probe tip 203 to deflect in a deflection direction that has a relationship to the movement of the user interface 231. Thus, motion of the user interface 231 in a given motion direction causes the microprocessor to generate deflection signals that cause the probe tip 203 to deflect in a deflection direction. The deflection direction can be the same as the motion direction. Alternatively, the microprocessor 237 can be programmed such that the deflection direction is angularly offset with respect to the motion direction. For instance, in some embodiments, it may be desirable for the deflection direction to be 180 degrees offset with respect to the motion direction, such that the motion direction and the deflection direction are inverted with respect to each other (for instance, if the probe is traveling down an inverted path in the anatomy). As described above, the guidance component 114 can further include a plurality of actuators 221 that are configured to cause the guide arms 210 of the probe to move in the proximal direction, thereby causing the probe tip 203 to deflect. The actuators are in communication with the microprocessor 237. Accordingly, the microprocessor 237 is configured to generate signals that cause the actuators 221 to, in turn, cause respective ones of the guide arms 210 to move in the proximal direction. The annulus 202 of the probe 200 can be attached to any suitable support structure, such as the user interface 231, and the guide arms 210 can be attached to the actuators 221, such that movement of the guide arms 210 in the proximal direction is with respect to the annulus 202, thereby causing the probe tip 203 to deflect. The annulus 202 can be detached from the user interface 231 so as to expose the lumen 205 of the probe 200. Lumen 205 can also be accessed while annulus 202 is attached and fixed to the user interface 231, through an access port 265 in the user interface 231. Thus, the user can remove and insert various surgical components 207 from and into the lumen 205 as desired, and can re-attach the annulus 202 to the user interface 231.

The guidance component 114 can further include a power source 239, a refresh input 240, and a deflection activation input 242 all in communication with the microprocessor 237. The deflection activation input 242 can be configured as a trigger switch 243. The refresh input 240 can be configured as a refresh switch 241 that can be separate from the trigger switch 243. Alternatively, the refresh switch 241 can be integrated with the trigger switch 243, such that actuation of the trigger switch likewise causes the motion sensor 233 to refresh its neutral position. Alternatively, the refresh input 240 can be any suitable alternative input, such as an operational condition as is described in more detail below. The guidance component 114 can further include a visible indicator light 244, which can be configured as a light emitting diode (LED). The trigger switch 243 can control activation and deactivation of deflection sensing. The refresh input is configured to change an initial frame of reference, and thus the neutral position, of the user interface 231. The guidance component 114 can further include a power supply, which can be configured as a battery, an interface to external power, or both. The power supply is configured to provide electrical power to all powered elements of the guidance component 114.

It should be appreciated that the microprocessor 237 receives input from the motion sensor 233, and further receives input from various other feedback system of the surgical system 100, such as the surgical component 207. The microprocessor 237 is further configured to process the input from the motion sensor 233 to achieve the correct deflection of the probe tip 203 as demanded by the movement of the user interface 231. The microprocessor 237 can control the actuators 221 to operate in accordance with any embodiment as desired. In one example, the microprocessor 237 can control the actuators 221 using current pulse width modulation, where the microprocessor 237 controls over a set amount of time a ratio or a percent of that time where a set voltage is running to the respective actuators 221 that are to be activated. For example, if the motion signals from the motion sensor 233 indicates a 45 degree tip deflection along only one actuator, and the microprocessor 237 is programmed such that 50% current flow achieves halfway deflection, then the maximum current will be impulsively applied (oscillating consecutively between on/applied current and off/no current) to the actuator 221 where the voltage is applied on average for a percentage of a given second suitable to achieve the indicated deflection, while no current flows to the actuator 221 during the remaining average time of the given second. It should be recognized, of course, that the current can pulse throughout the duration of the given second to arrive at the desired proportion of the time that the voltage is applied, and the desired proportion of the time that no current is applied. It should thus be appreciated that the microprocessor 237 can generate signals that cause the probe tip 203 to deflect a distance proportional to the amount of movement of the motion sensor 233. Thus, greater amounts of movement of the user interface 231 produces proportional increasing amounts of deflection of the probe tip 203 up to a maximum deflection.

With continuing reference to FIGS. 10A-10B, operation of the user interface 231 will now be described. It should be appreciated that the control system 110 can be configured such that the guidance component can be integrated into the user interface as a single unit, thereby allowing operation of the user interface with one hand, while the other hand manually introduces the probe 200 into the patient. It is appreciated that the patient can be human or a non-human animal, such as a quadruped. In one example, the probe 200 can be introduced into the vasculature of a patient, or toward a non-vascular anatomical structure. In another example, non-vascular anatomical structure can be accessed through an accessible lumen, gap, or space in tissue which can provide a path to the target anatomy.

To activate the user interface 231, the power source 239 can be activated, which causes power to flow to the various powered elements of the guidance component 114. The indicator light 244 can turn a first color, such as blue, to indicate that the user interface 231 has been powered on. Next, once it is desired to deflect the probe tip 203, the user actuates the deflection activation input 242, for instance by applying a force to the trigger switch 243 so as to actuate the trigger switch 243 from an open position to a closed position. For instance, a compressive force can be applied to the trigger switch 243 to actuate the trigger switch 243 to the closed position. When the deflection activation input 242 is in the closed position, an electrical deflection circuit is correspondingly closed between the power supply, the microprocessor 237, and the actuators 221. The actuators 221 can be configured to apply a mechanical pull force to the guide arms, for instance when the guide arms 210 define pull wires. In one embodiment, the actuators 221 can be configured as servo motors or any suitable alternative device capable of providing the mechanical pull force. Alternatively, the actuators 221 can be configured as current flow regulators when the guide arms 210 include the shape memory material 215. In this regard, it should be appreciated that the current flow regulators can be integrated into the microprocessor as desired. The visible indicator lights 244 can display a second color, such as green, to indicate that movement of the user interface 231 will cause deflection of the probe tip 203. When the deflection activation input 242 is in the open position, the electrical deflection circuit is open and prevents movement of the user interface 231 from causing the probe tip 203 to deflect.

When the electrical deflection circuit is closed, movement of the user interface 231 in any direction as desired will produce an identical or ratio-based response at the probe tip 203. In particular, the direction and amount of movement of the user interface 231 will be sensed by the motion sensor 233, and the microprocessor 237 will determine the amount and direction that the probe tip 203 is to deflect with respect to the probe body 201. In particular, if the actuators 221 are current flow regulators, such as variable resistors, the microprocessor 237 receives the motion signals from the motion sensor 233 and determines, from the motion signals, the appropriate amount of current and its duration in the one or more variable resistors. Thus, the resistors, start, stop, and vary electrical current applied to the respective guide arms 210 at a rate set by the microprocessor 237, and sends a pulsating current down the guide arm so that the corresponding shape memory material 215 deflects in the manner described above. Based on the variable resistors selected to apply current to the guide arms, the proportional amount of current applied by the selected variable resistors, and the resulting shape memory wire temperature to be reached, a predetermined direction and amount of deflection of the probe tip 203 can be obtained.

During operation, the electrical current applied to the shape memory material 215 causes the temperature of the shape memory material 215 to increase. In this regard, the shape memory material 215 can function as an electrical resistor. The shape memory material responds to the increased temperature by changing its molecular configuration, causing it to compress along its length, thereby reducing its length. With both ends of the shape memory material 215 fixed, such that at least a portion of the shape memory material 215 is spaced from the central axis of the probe 200 in a respective direction, the compression causes a force that biases the probe tip 203 to mechanically deflect in the respective direction. Thus, the amount of the compression of the shape memory material 215, and thus the amount of the biasing force, is directly related to the temperature of the shape memory material. The biasing force can be changed, held constant, or reversed at any time depending on the temperature of the shape memory material 215, which is directly related to the flow of current as determined by the microprocessor 237.

If desired, the control system 110 can include a temperature feedback loop that includes at least one temperature sensor 247 (see FIG. 2) in communication with the microprocessor 237. The temperature sensors 247 are configured to measure the temperature of respective ones of the shape memory material 215, and communicate the measured temperature to the microprocessor 237. Thus, the microprocessor 237 can determine the exact temperature of the shape memory material and know exactly which temperature to reach to meet desired deflection indirectly by controlling current. Further, the control system 110 can include a deflection feedback loop that includes at least one position sensor 248 (see FIG. 2) at the probe tip 203 that is in communication with the microprocessor 237. The position sensor 248 is configured to measure the deflection of the probe tip 203 and communicate the measured deflection to the microprocessor 237, whether the guide arms 210 are configured as pull wires or include shape memory material. Thus, the microprocessor 237 can determine the both the exact temperature of the shape memory material 215 of the guide arms 210 when the guide arms 210 include a shape memory material. The microprocessor 237 can further determine the exact amount and direction of associated deflection of the probe tip 203. Thus, the microprocessor 237 can correlate the amount of deflection of the probe tip 203 to the deflection signals that the microprocessor provides the actuators 221, and calibrate the actuators 221 accordingly.

The annulus 202 can be made from a thermoset material as opposed to a thermoplastic to so as to substantially eliminate the possibility of the probe 200 warping under increased heat at specific points in thermal communication with the shape memory material 215. Though the outer surface of the annulus 202 will not increase temperature greater than 3-5 degrees Celsius and pose no biological harm, the shape memory material 215 has the potential to greatly increase in temperature as described above. A thermoset material will not warp or compromise its ability to bend and hold shape at any temperature under its melting point (melting point usually greater than 300 degrees Celsius and of no concern to be reached with the shape memory material 215).

Just as an increase in temperature of the shape memory material 215 causes the shape memory material 215 to contract along its length from a first length to a second length that is less than the first length, cooling of the shape memory material 215 or a counter acting force (the tubing material trying to move back to its resting state) causes the shape memory material to relax and return to a position toward its first length. Thus, the frequency of applied current to the shape memory material 215 can be decreased so as to decrease the amount of deflection of the probe tip 203 in the respective direction defined by the shape memory material relative to the central axis of the probe 200. Alternatively, current flow to the shape memory material 215 can be terminated so as to return the shape memory material 215 to its first length. Further, the small diameters of the shape memory material wires can cause a high level of concentration of thermodynamic output while dissipating heat at a quick rate as it cools. In one embodiment, the probe can include a lumen that is filled with a coolant such as water, glycine, or a similar fluid, having a high heat capacity in thermal communication with a corresponding one or more of the shape memory materials 215. The lumen can extend through the annulus 202 or any other location as desired. Further, surrounding blood and other anatomical water/fluids can provide a secondary source of heat removal from the shape memory material 215.

If, on the other hand, the actuators 221 are servo motors, then the microprocessor, from the motion signals, determines the appropriate amount of rotation in one or more selected ones of the servo motors. Based on the selected servo motors, and the amount of proportional rotation of each of the respective servo arms 229, a predetermined direction and amount of deflection of the probe tip 203 can be obtained. In particular, the deflection of the probe tip 203 is directly controlled by the selected servo motors, and the length that the guide arms 210 are pulled in the proximal direction from their neutral position. As described above, the other guide arms 210 can passively or actively be translated in the distal direction from their neutral position. The durometer change in the annulus 202 determines the location of the deflection of the probe tip 203. The probe tip 203 can be returned to its non-deflected state by returning the guide arms 210 to their neutral positions.

During operation, once the probe tip 203 has deflected its desired amount from the neutral position, and it is desired to return the probe tip 203 to its neutral position, the trigger switch 243 can be released, and the second light would turn off and be replaced by the first light. Next, if desired, the power source 239 can be deactivated, thereby removing power to the powered elements of the guidance component 114. In one embodiment, the neutral position of the probe tip 203 can be a position whereby the probe tip has zero deflection, and is inline with the central axis of the probe 200. As described above, the control system 110 can include a refresh input 240 that is in communication with the microprocessor 237. Actuation of the refresh input 240 causes the current position and orientation of the user interface 231 to be a new neutral position of the user interface 231. Further motion of the user interface 231 with respect to the new neutral position will cause the microprocessor 237 to generate deflection signals, in the manner described above, that correspond to motion of the user interface 231 with respect to the new neutral position. In this regard, it is recognized that physicians are accustomed to spending precious operating room time dealing with changes in the frame of reference of their deflection/vessel navigation systems as they navigate through the anatomy. For instance, when attempting to navigate a conventional catheter into the inferior vena cava from the groin region. Once the catheter tip reaches the inferior vena cava junction, and deflects towards the right atrium and eventual deflects inward towards the right ventricle, the catheter tip is changing direction between 10 to 180 degrees. Also, consider the varying angles in which the probe rotates unitedly due to resistance by the tissues and traversing through turbulent anatomy. Considering the central axis, the position of the probe tip usually arrives at a different angle than its orientation when inserted through skin in addition to the previously mentioned direction change. While fluoroscopic imaging can show the change, the conventional user interface for the catheter stays stationary at a fixed point on the catheter end, and the physician must therefore readapt his thinking to the situation. Actuation of the refresh input 240 allows the physician to move the free floating user interface 231 to a moved position that is better aligned with the physician's personal frame of reference with respect to the probe tip 203, and actuate the refresh input 240 to reset the accelerometers 235 to a neutral position when the interface is at the moved position.

The refresh input 240 can be configured as a refresh switch 241 such that activation of the switch causes the microprocessor to identify the current position of the user interface 231 as a neutral position, such that movement of the user interface 231 with respect to the neutral position will cause the probe tip 203 to deflect in the manner described above. Alternatively, the refresh input can be an operational condition. For instance, the refresh input can be actuated when the user interface is set onto a flat surface, or placed in proximity of an external refresh sensor apparatus, which can for instance be configured as a base of the guidance component 114 as described in more detail below, or when the probe tip 203 has achieved a threshold amount of deflection. The visible indicator light 244 can turn a third color, such as purple, to indicate that the refresh input 240 has been actuated.

In the event of an unexpected electrical power outage to the surgical system 100, the probe tip 203 can be sufficiently flexible that the probe 200 can be safely removed from the anatomical structure. Further, it is recognized that when the actuators 221 are configured to apply current to the shape memory material 215, the applied current is removed in the event of a power failure, which causes deflection of the probe tip 203 to abate. Alternatively still, when the actuators 221 are configured as servo motors, the servo motors can be manually accessed and returned to their respective neutral positions or any suitable alternative position as desired.

As described above, navigation of the probe 200 to the target anatomical location can be viewed under fluoroscopic imaging to assist the physician in navigational guidance. The user interface 231 can also provide feedback to the physician when the probe tip 203 has contacted an anatomical structure, such as soft tissue, vascular wall, bone, organ, or the like. For instance, the probe tip 203 can carry one or more pressure sensors 245 (see FIG. 2) that are in communication with the microprocessor 237. The user interface 231 can further include a feedback actuator 246 that is in communication with the microprocessor 237. During operation, when the probe tip 203 has contacted an anatomical structure, the contact is sensed by one or more of the pressure sensors 245, which sends a signal to the microprocessor. The signal can be transmitted over a communication line to the microprocessor 237 or can travel wirelessly to the microprocessor 237. In response to the signal from the one or more of the pressure sensors 245, the microprocessor 237 actuates the feedback actuator 246 to provide feedback to the operator that the probe tip 203 has contacted the anatomical structure. The feedback actuator 246 can be configured as a haptic feedback actuator such as vibrator, a rotating mass, an audible feedback actuator such as an alarm, or a visual feedback actuator such as an indicator capable of being sensed by the operator of the user interface 231.

In accordance with one embodiment, the annulus 202 can be anchored to the user interface 231, and the guide arms 210 can be attached to respective actuators carried by the user interface 231 as described above. Thus, the deflection control signals generated by the microprocessor 237 can travel to the actuators 221 by a wired communication line. Alternatively, as illustrated in FIG. 10B, the deflection signals generated by the microprocessor 237 can travel wirelessly to the actuators 221. Similarly, as described above, the user interface 231 can carry the surgical controls 116 (see FIG. 1A) that control the surgical component 207. The surgical controls 116 can be in communication with the microprocessor 237. For instance, the surgical controls 116 can be wired to the microprocessor 237, or can communicate wirelessly with the microprocessor 237. Further, as illustrated in FIGS. 10A-10B, it is recognized that the various elements of the guidance component 114, including the microprocessor 237, the motion sensor 233, the actuators 221, the power source 239, the refresh input 240, and the deflection activation input 242, can be carried by the user interface 231 in the manner described above, or can be located anywhere external to the user interface 231 as desired. It should be further appreciated that the controls for the surgical component and/or imaging component can also be installed on the user interface or elsewhere as desired.

Referring, for instance, to FIG. 11, the guidance component 114, and thus the control system 110, can include the user interface 231, and can further include a base unit 249 that is separate from the user interface 231 and is attached to the probe 200. The base unit 249 can include the actuators 221 that are attached to the guide arms 210 in the manner described above, and the annulus 202 can be attached to the base unit 249, such that movement of the guide arms 210 is with respect to the annulus 202 so as to cause deflection of the probe tip 203 in the manner described above. The motion sensor 233 and microprocessor 237 can be carried by the user interface 231 as described above. Further, the user interface 231 can include a transceiver 251 that is in communication with the microprocessor 237. Similarly, the base unit 249 can include a transceiver 251 that is in communication with the actuators 221 and also in communication with the pressure sensor 245. The transceiver 251 of the user interface 231 is configured to transmit wireless signals to the transceiver 251 of the base unit 249, and is further configured to receive wireless signals from the transceiver 251 of the base unit 249. Similarly, the transceiver 251 of the base unit 249 is configured to transmit wireless signals to the transceiver 251 of the user interface 231, and is further configured to receive wireless signals from the transceiver 251 of the user interface 231. The wireless signals can be Bluetooth, cellular, Wi-Fi, or any suitable alternative wireless signal.

During operation, the microprocessor 237 can receive movement signals from the motion sensor 233 as described above. Instead of sending the deflection signals to the actuators 221 over wires, the microprocessor 237 can send wireless deflection signals to the actuators 221 of the base unit 249. Further, the base unit 249 can send signals from the pressure sensors 245, temperature sensors 247, and position sensors 248 wirelessly to the microprocessor 237 of the user interface 231, to be processed by the microprocessor 237 in the manner described above.

Alternatively still, referring to FIG. 12, the microprocessor 237 can be carried by the base unit 249, and the base unit 249 can further carry an external motion sensor 253 that is external to the user interface 231. The external motion sensor 253 can measure the position and orientation of the user interface 231 using any suitable technology as desired. For instance, the external motion sensor 253 can be an optical sensor, such as a video camera whose output can be analyzed by the microprocessor 237 in order to determine movement of the user interface 231. Alternatively, the external motion sensor 253 can be an active or passive infrared sensor that senses movement of user interface. Alternatively, the external motion sensor 253 can apply radar, microwave, or tomographic motion detection of the user interface 231. Alternatively, the external motion sensor 253 can include a microphone and acoustic sensors to measure the acoustics associated with movement of the user interface 231. Alternatively, the external motion sensor 253 can be a magnetic sensor and magnetometer, and the user interface 231 can carry a magnetic source, such that the external motion sensor 253 detects changes in magnetism of the user interface 231 to detect motion of the user interface 231. Alternatively, the external motion sensor 253 can be a GPS device that receives receive global positioning signals that identify changes of position of the user interface 231. In this regard, it should be appreciated that some embodiments of the external motion sensor can be configured as a motion sensor that is internal to the user interface 231. The external motion sensor 253 can send the motion signals to the microprocessor 237, which in turn sends deflection signals to the actuators 221 in the manner described above. Alternatively, the user interface 231 can include a motion sensor 233 that generates motion signals in the manner described above, and sends wireless motion signals to the microprocessor 237 of the base unit. The microprocessor 237 can further send feedback data to the feedback actuator 246 of the user interface 231 in the manner described above.

Figure 13:
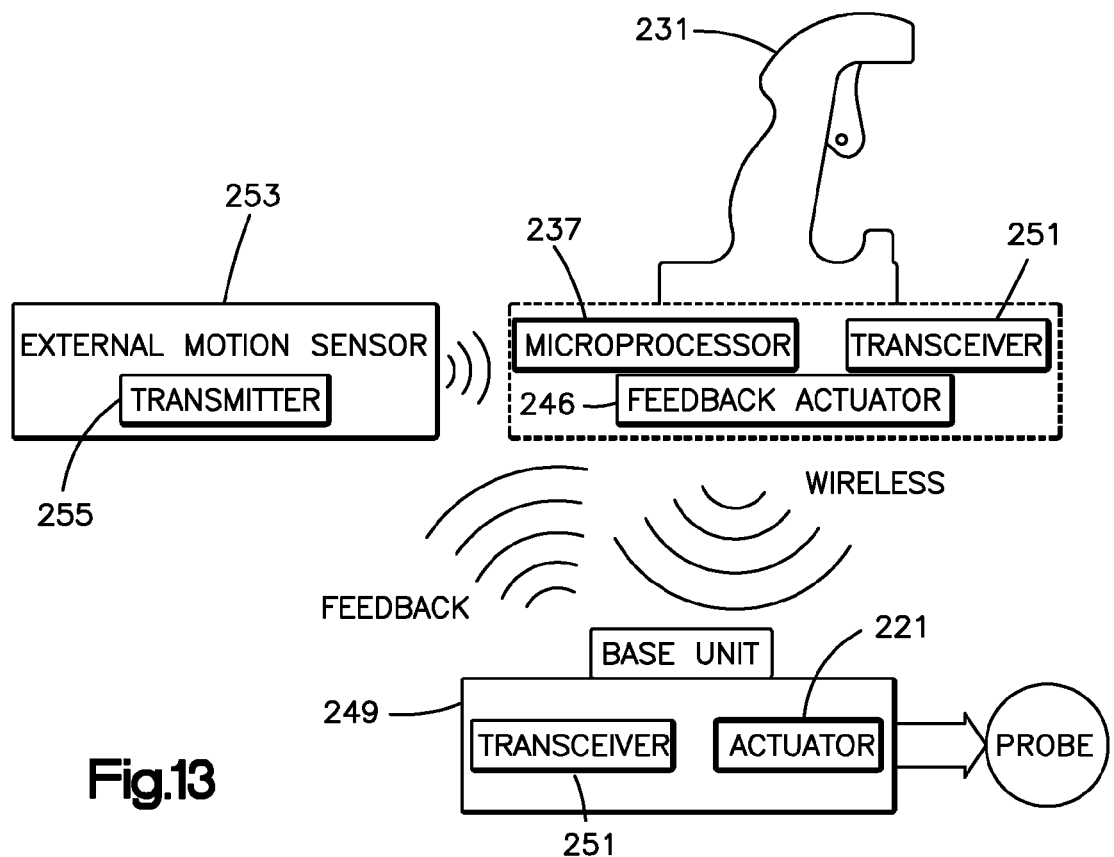
FIG. 13 is a schematic view of the guidance component similar to FIG. 12, but constructed in accordance with an alternative embodiment.

Referring now to FIG. 13, the external motion sensor 253 can be external to both the user interface 231 and the base unit 249. Thus, the external motion sensor 253 can sense motion of the user interface 231 in the manner described above, and can communicate the motion signals wirelessly via a transmitter 255 to the microprocessor 237 that is carried by the user interface 231. The microprocessor 237 can, in response to the motion signals, generate deflection signals in the manner described above. The deflection signals are communicated wirelessly to the actuators 221 that are carried by the base unit 249.

Figure 14:
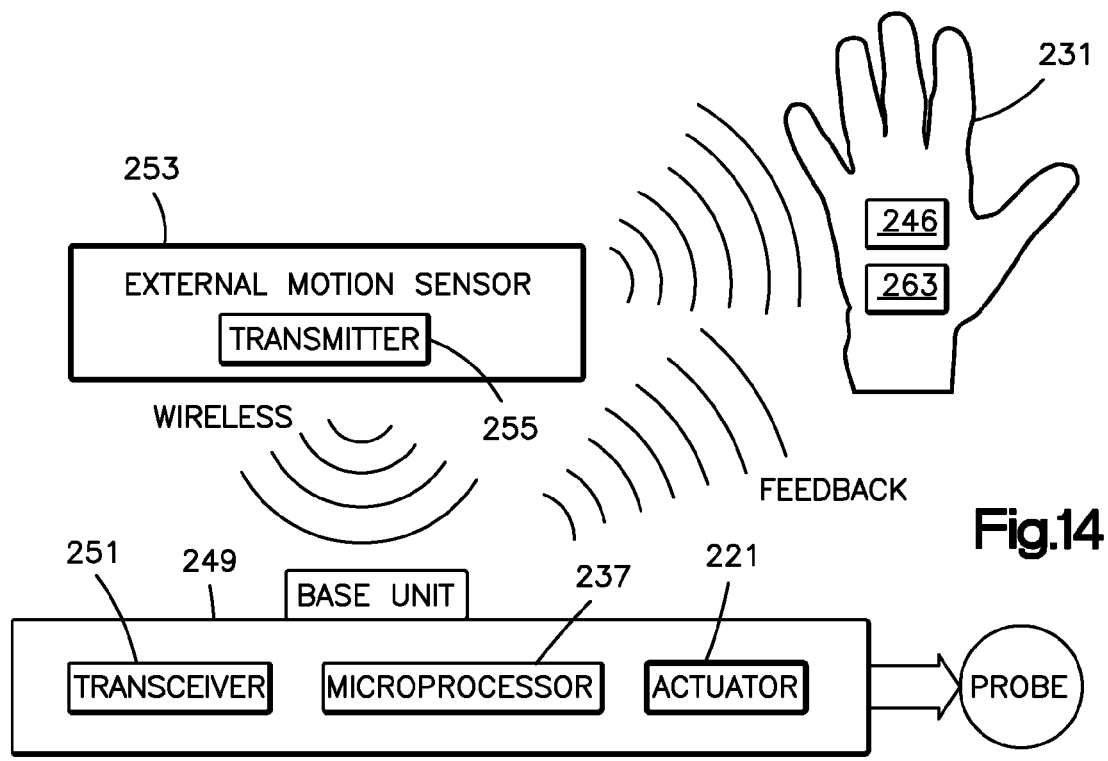
FIG. 14 is a schematic view of the guidance component similar to FIG. 13, but constructed in accordance with an alternative embodiment.

Finally, referring to FIG. 14, the user interface 231 be configured as a substrate that can be carried by the user's hand. For instance, the user interface 231 can be configured as a glove that can be worn by the user's hand, a stylus, or any suitable alternative apparatus. The guidance component 114 can include the external motion sensor 253 that is external to the user interface 231. The external motion sensor 253 can further be external to the base unit 249, or can be carried by the base unit 249. The base unit 249 can include the microprocessor, the actuators, the visible indicator light 244, the refresh input, the power source 239, and the deflection activation input 242. In the event that the external motion sensor 253 is external to the base unit 249, the external motion sensor 253 can communicate the motion signals wirelessly to the microprocessor 237 on the base unit 249. The microprocessor 237 can operate in the manner described above in response to the motion signals. Thus, the external motion sensor can wirelessly transmit the motion signals to a transceiver 251 or other suitable receiver of the base unit 237. During operation, the microprocessor 237 can receive input from the pressure sensors, as described above, and transmit signals from the transceiver 251 or other suitable transmitter to the feedback actuator that is carried by the user interface 231, in the manner described above. Further, the user interface 231 can include a receiver 263 that receives feedback signals from the base unit 249 so as to actuate the feedback actuator 246 carried by the user interface 231 in the manner described above. Further, the base unit 249 can define a motion zone within a predetermined proximity of the base unit 249. Thus, when the user interface 231 is moved to a position within the motion zone (or from a position within the motion zone to a position outside the motion zone), the refresh input can be actuated, such that the position of the user interface 231 as detected by the external motion sensor 253 is deemed to be in the neutral position.

Referring now to FIGS. 2 and 5 and 15-17, and as described above, the lumen 205 of the probe 200 is configured to carry a surgical component 207, which can be any component as desired. Additional details of one example of the surgical component 207 are shown in FIGS. 2 and 15-17. The surgical component 207 can include a surgical device 208 within the annulus 202 and between the transducers 206. The surgical device 208 communicates with the control system 110 through the communication line 214. A surgical member 216 extends through the tubular member 204. The surgical member 216 is substantially formed from a flexible hollow tube that is attached to a container 213 outside the patient's body. The tubular section of the surgical member 216 carries materials such as drugs stored in the container 213 to the surgical device 208 and carries suctioned materials such as body fluid out of the surgical device 208 to the container 213.

The surgical device 208 includes a surgical device body 218 defining an interior 220 of the surgical device 208. The surgical device body 218 is shown by itself in FIG. 15 and containing its operational components in FIG. 16. The body 208 includes an open interior window 224 surrounded by seal surfaces 222 that are coated with a biocompatible material capable of forming a substantially liquid-tight seal when pressed against a vessel wall as shown in FIG. 16. The window 224 allows the surgical member 216 to access to the vessel wall.

Operational components of the surgical device 208 are best shown in FIG. 16. The surgical member 216 extends from the tubular member 204 into a tubular junction 226, which in this example, is T-shaped. The surgical tip 228 may either be directed downwardly through the junction 226 or laterally. The shape of the tubular junction may vary, depending on the embodiment. In another example, the tubular junction is J-shaped. The surgical device 208 is preferably small enough to allow at least one-quarter of the inner diameter of the vessel open so that the vessel is not completely occluded.

A vessel sealant material 228 is positioned near the bottom of the junction 226 and is mechanically connected to a motor 230 or the like that is capable of moving the vessel sealant material 228 into the bottom of junction 216 when the user desires to seal a hole in the vessel wall. Preferably, the sealant material is made of biocompatible heat activated material that shrinks when heated and seals both sides of the hole like a rivet. The sealant material may be made of a collagenous material such as collagen or the like.

If desired, the surgical device 208 may also include one or more temperature and/or pressure sensors.

When the probe 200 is positioned in the desired area of the body, seal surfaces 222 may be held in place using a positioning member 232 that presses against the vessel wall when activated. The positioning member 232 includes positioning material 234 on the exterior of the body 218 and fed through a hole 236 into the surgical device 208. A gear 238 contacts the positioning material 234 and, when the gear turns by rotation of the external screw-like thread 254 on conical body 250 via direct contact with gear 238 in the upper left portion of junction 226, the resulting force deforms the positioning material 234 causing it to extend outwardly. When the gear 238 is reversed by reverse rotation of external screw-like thread 254, the positioning material 234 reverts to its original position un-securing the probe 200 and the seal surfaces 222 from the vessel wall.

Referring now to FIG. 17 the surgical member 208 includes a multifunction surgical tip 250 having a conical body 250. The conical body 250 includes external screw-like threads 254 and internal screw-like threads 256 having the opposite handedness as the external screw-like threads 254. Rotating the conical body 250 one direction allows the external screw-like threads 254 to cut through bodily material in a screw-like manner. If the direction of rotation is reversed, however, the internal screw-like threads 256 can retain a sample of the bodily material for examination. Rotation can be achieved manually or via a motor-type device on the surgical member 216. These threads 254, 256 form screw-like pathways that direct capillary action during injection and suction.

To operate on an area of the body that is outside the vessel, the surgical tip 250 is used to form a hole in the vessel wall. The hole may be formed several different ways. For example, the surgical tip 250 may be inserted through the vessel wall. Alternatively, the vessel may be punctured by activating electrical leads 258 on the surgical tip 250. By adding suction to the surgical member 216, bodily material can be suctioned through the surgical tip 250 to the container 213. Drugs or other therapeutic substances can be delivered through the surgical tip 250 by pumping the substance(s) through the surgical member 216 from the container 213.

When the procedure is finished, the hole in the vessel wall may be sealed using the vessel sealant material 228. This is achieved by activating the motor 230, which moves the sealant material 228 into the bottom of the junction 226. The user may then push the sealant material 228 into the hole using the surgical tip 250. The sealant material 228 fills the hole, preventing bleeding. The electrical leads 258 on the surgical tip 250 can be used to cauterize the sealant material 228, activating its heat shrink properties that fuse both sides of the hole similar to a rivet.

Guide arms 260 that function similarly to those previously described are positioned near the surgical tip 250 to allow the user to place the surgical tip 250 at the desired position outside the vessel.

Another example of a surgical procedure available for use with the probe 200 is a cardiac ablation study. Conventional methods involve the destruction of specific regions of cardiac tissue with a crude one-directional or bi-directional catheter. The probe 200 allows for omni-directional steerability in the manner described above, thereby rendering the ablation process easier, faster, and results in more reliable alignment with the target tissue to be ablaited.

In another procedure, the surgical component 207 can be an endoscope for urologists to use during a Ureteroscopy. Conventional methods suffer from a lack deflection control of endoscopes in more than one plane, which causes the urologist to spend precious time trying to move the endoscope while being limited to what quadrants of the kidney are accessible to remove tumors, laser ablait kidney stones, and/or to visually examine these quadrants. The probe 200 allows urologists a solution to provide complete 3 axis control which saves time, money, and increases overall effectiveness. Further, the small size of the probe 200 can ensure that the probe 200 and endoscope will not get stuck in the ureter (a common uerteroscopy problem) as compared to current larger mechanical endoscopy systems.

In another example, podiatrists lack suitable steer-ability during conventional arthroscopic ankle procedures. For instance, when trying to clear out scar tissue and other bodily issue around the ankle joint, the surgeon typically uses a stiff metallic like rod. Though the rod is sufficient to clear out the anterior region, it does not provide direct access to the posterior region given the curvature of the ankle bone. As a result, the conventional approach is to drill into the tibia at a sufficient angle to clear the curvature of the ankle bone. Even then, however, the ability to clear out as much as what can be done on the anterior region is reduced. The deflectable probe tip 203 allows podiatrists to steer the probe 200 around the curved ankle bone and prevent unnecessary damage to patients.

In yet another example, vascular trauma surgeons performing an emergency fasciotomy to remove a dangerous blood clot in the leg usually make deep cuts along substantially the entire length of the calf to gain access to blood vessels. The surgical component 207 carried by the probe can be a hook like system, and the probe tip 203 can deflect along a guide path through a small minimally invasive incision of the calf to the blood clot, such that the hook can remove the blood clot.

The foregoing description is provided for the purpose of explanation and is not to be construed as limiting the surgical system. While various embodiments have been described with reference to preferred embodiments or preferred methods, it is understood that the words which have been used herein are words of description and illustration, rather than words of limitation. Furthermore, although the embodiments have been described herein with reference to particular structure, methods, and embodiments, the electrical connector is not intended to be limited to the particulars disclosed herein. For instance, it should be appreciated that structure and methods described in association with one embodiment are equally applicable to all other embodiments described herein unless otherwise indicated. Those skilled in the relevant art, having the benefit of the teachings of this specification, may effect numerous modifications to the electrical connector as described herein, and changes may be made without departing from the spirit and scope of the electrical connector, for instance as set forth by the appended claims.

What is claimed:

1. A control system for a surgical probe, the control system comprising:
   a user interface;
   a motion sensor configured to detect movement of the user interface and generates motion signals in response to the detected movement,
   a processor configured to receive the motion signals from the motion sensor, and in response generates real-time deflection signals that correspond to the received motion signals; and
   a plurality of actuators each in communication with the processor, wherein the actuators are configured to be coupled to the surgical probe, wherein the actuators are configured to receive the deflection signals and, in turn, cause a tip of the surgical probe to deflect, and a refresh input that causes a moved position and orientation of the user interface, with respect to a previous position and orientation of the user interface, to be a new neutral position of the user interface, such that movement of the user interface with respect to the new neutral position is detected by the motion sensor that generates motion signals in response to the detected movement of the user interface with respect to the new neutral position, and the processor receives from the motion sensor the motion signals in response to the detected movement of the user interface with respect to the new neutral position, and in response generates real-time deflection signals that correspond to the received motion signals.

2. The control system as recited in claim 1, wherein the actuators comprise servos that move in response to the deflection signals.

3. The control system as recited in claim 1, wherein the actuators comprise current flow regulators that are configured to, in response to the deflection signals, apply a electrical current to the surgical probe.

4. The control system as recited in claim 1, wherein the refresh input comprises a refresh switch carried by the user interface.

5. The control system as recited in claim 4, further comprising a deflection activation input that is configured to be actuated so as to cause the processor to detect the movement of the user interface.

6. The control system as recited in claim 5, wherein the deflection activation input is a switch of the user interface, and the switch further defines the refresh input.

7. The control system as recited in claim 1, wherein the processor and motion sensor are carried by the user interface.

8. The control system as recited in claim 7, wherein the motion sensor comprises an accelerometer.

9. The control system as recited in claim 1, wherein the control system further comprises a base unit that is separate from the user interface, and the actuators are carried in the base unit, and the processor sends the deflection signals wirelessly to the actuator.

10. The control system as recited in claim 9, wherein the motion sensor is external to the user interface and sends the motion signals wirelessly to the processor.

11. The control system as recited in claim 1, wherein the processor is carried by the user interface.

12. The control system as recited in claim 10, wherein the processor is carried by the base unit.

13. The control system as recited in claim 1, further comprising a stationary base, wherein the user interface is a free floating user interface having six degrees of freedom with respect to the stationary base, and the movement of the user interface is with respect to the stationary base.

14. The control system as recited in claim 1, wherein movement of the user interface in any direction with respect to the new neutral position produces an identical response at the tip of the surgical probe.

15. The control system as recited in claim 1, wherein movement of the user interface in any direction with respect to the new neutral position produces a ratio-based response at the tip of the surgical probe.

16. The control system as recited in claim 2, wherein the servos have-servo arms that move in response to the deflection signals.

17. The control system as recited in claim 6, wherein the switch of the user interface is a trigger switch, and the trigger switch further defines the refresh input.

* * * * *